(12) United States Patent
Yarger

(10) Patent No.: US 8,168,621 B2
(45) Date of Patent: May 1, 2012

(54) 6-SUBSTITUTED ESTRADIOL DERIVATIVES AND METHODS OF USE

(75) Inventor: James Yarger, Cedarburg, WI (US)

(73) Assignee: Endece, LLC, Mequon, WI (US)

( * ) Notice: Subject to any disclaimer, the term of this patent is extended or adjusted under 35 U.S.C. 154(b) by 889 days.

(21) Appl. No.: 12/132,857

(22) Filed: Jun. 4, 2008

(65) Prior Publication Data

US 2008/0312202 A1    Dec. 18, 2008

Related U.S. Application Data

(63) Continuation-in-part of application No. 11/947,645, filed on Nov. 29, 2007, and a continuation-in-part of application No. 11/541,987, filed on Oct. 2, 2006, now Pat. No. 7,846,918.

(60) Provisional application No. 60/867,980, filed on Nov. 30, 2006, provisional application No. 60/722,204, filed on Sep. 30, 2005.

(51) Int. Cl.
    *A61K 31/56*     (2006.01)
    *C07J 1/00*     (2006.01)

(52) U.S. Cl. .......................... 514/182; 514/178; 552/626

(58) Field of Classification Search ................... 552/626
See application file for complete search history.

(56) References Cited

U.S. PATENT DOCUMENTS

| | | | |
|---|---|---|---|
| 4,840,943 A | 6/1989 | Buzzetti et al. | |
| 5,892,069 A | 4/1999 | D'Amato et al. | |
| 6,239,123 B1 | 5/2001 | Green | |
| 6,784,170 B2 | 8/2004 | Peters et al. | |
| 2003/0055029 A1 | 3/2003 | D'Amato et al. | |
| 2005/0014737 A1 | 1/2005 | Agoston et al. | |
| 2005/0192263 A1 | 9/2005 | Meeinger et al. | |
| 2006/0009434 A1 | 1/2006 | Hillisch et al. | |
| 2008/0119447 A1 | 5/2008 | Yarger | |

FOREIGN PATENT DOCUMENTS

| | | |
|---|---|---|
| JP | 07-215992 | 8/1995 |
| WO | 02/22645 | 3/2002 |
| WO | WO 2007/041564 A3 | 4/2007 |

OTHER PUBLICATIONS

International Search Report and Written Opinion issued for PCT/US09/46120.
M. Adamczyk et al., An Efficient stereoselective synthesis of 6-alpha-aminoestradiol: Preparation of estradiol fluorescent probes, Steroids, 1997, 462-467, 62.
M. R. Tremblay et al, Inhibitors of type 1 17beta-hydroxysteroid dehydrogenase with reduced estrogenic activity: Modifications of the positions 3 and 6 of estradiol, Journal of Enzyme Inhibition and Medicinal Chemistry, Apr. 2005, 153-163, 20(2).
M. Dutertre et al., Molecular Mechanisms of Selective Estrogen Receptor Modulator (SERM) Action, JPET, 2000, 431-437, 295.
B. T. Zhu et al., Quantitative Structure-Activity Relationship of Various Endogenous Estrogen Metabolites for Human Estrogen Receptor alpha and beta Subtypes: Insights into the Structural Determinants Favoring a Differential Subtype Binding, Endocrinology, 2006, 4132-4150, 147(9).
S. Top et al., Stereospecific 6-Alkylation of Oestradiol Derivatives via Cr(C))3 Complexes, J. Chem. Soc., Chem. Commun., 1984, 428-429.
M. Numazawa et al., Structure-activity relationships of 2-, 4-, or 6-substituted estrogens as aromatase inhibitors, Journal of Steroid Biochemistry & Molecular Biology, 2005, 51-58, 96.
M. Numazawa et al., Studies on the catalytic function of aromatase: aromatization of 6-alkoxy-substituted androgens, Journal of Steroid Biochemistry & Molecular Biology, 2002, 65-73, 82.
M. Adamczyk et al., Synthesis of 6beta-[2'-Aminoethyl)carboxamidomethyl]estradiol and Preparation of Estradiol Probes, Bioconjugate Chem., 1998, 403-408, 9.
S. Itoh et al., Synthesis of Oligodeoxynucleotides Containing a Single 6alpha- or 6beta-Diastereoisomer of N2-(Estradiol-6-yl)-2'-deoxyguanosine, Chem. Res. Toxicol., 2006, 450-456, 19.
International Preliminary Report on patentability issued on PCT/US2007/85913.
Cadot, et al., "C6-(N,N-butyl-methyl-heptanamide) derivatives of estrone and estradiol as inhibitors of type 1 17β-hydroxysteroid dehydrogenase: Chemical synthesis and biological evaluation", Bioorganic & Medicinal Chemistry, 2007, pp. 714-726, vol. 15.
Numazawa, M. et al. "Synthesis and structure-activity relationships of 6-phenylaliphatic-sutbsituted C19 steroids having a 1,4-diens, 4,6-diene, or 1,4,6-triene structure as aromatase inhibitors." Steroids, Mar. 1999, vol. 64, pp. 187-196.
Numazawa, M. et al. "Inhibition of estrone sulfatase by aromatase inhibitor-based estrogen 3-sulfamates." Steroids, May 2006, vol. 71, pp. 371-379.

*Primary Examiner* — Barbara P Badio
(74) *Attorney, Agent, or Firm* — Reinhart Boerner Van Deuren s.c.

(57) ABSTRACT

A compound having the structure:

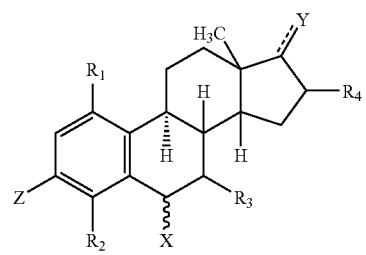

wherein $R_1$, $R_2$, R, R, X, Y and Z are as defined herein. The compounds are estrogen receptor modulators useful for the treatment of proliferative disorders.

3 Claims, 8 Drawing Sheets

Figure 1. Estradiol Biosynthetic Pathway
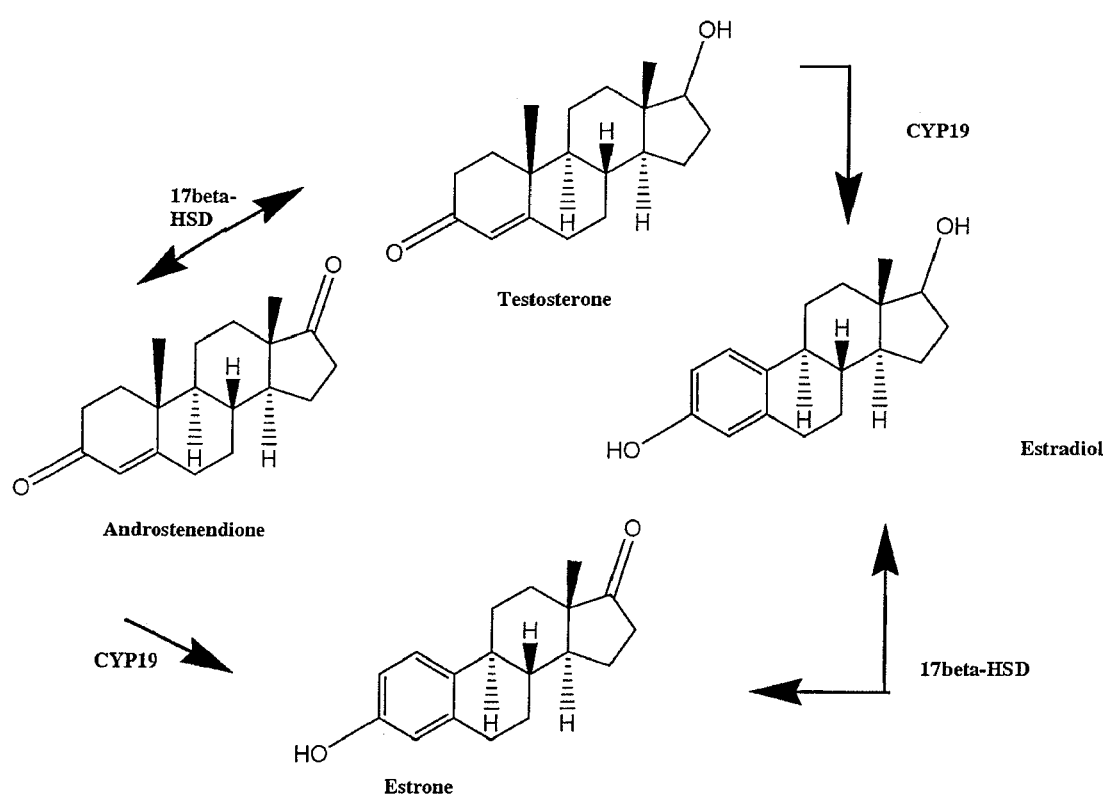

Figure 2. Predicted Metabolic Pathway of the Presented Compounds
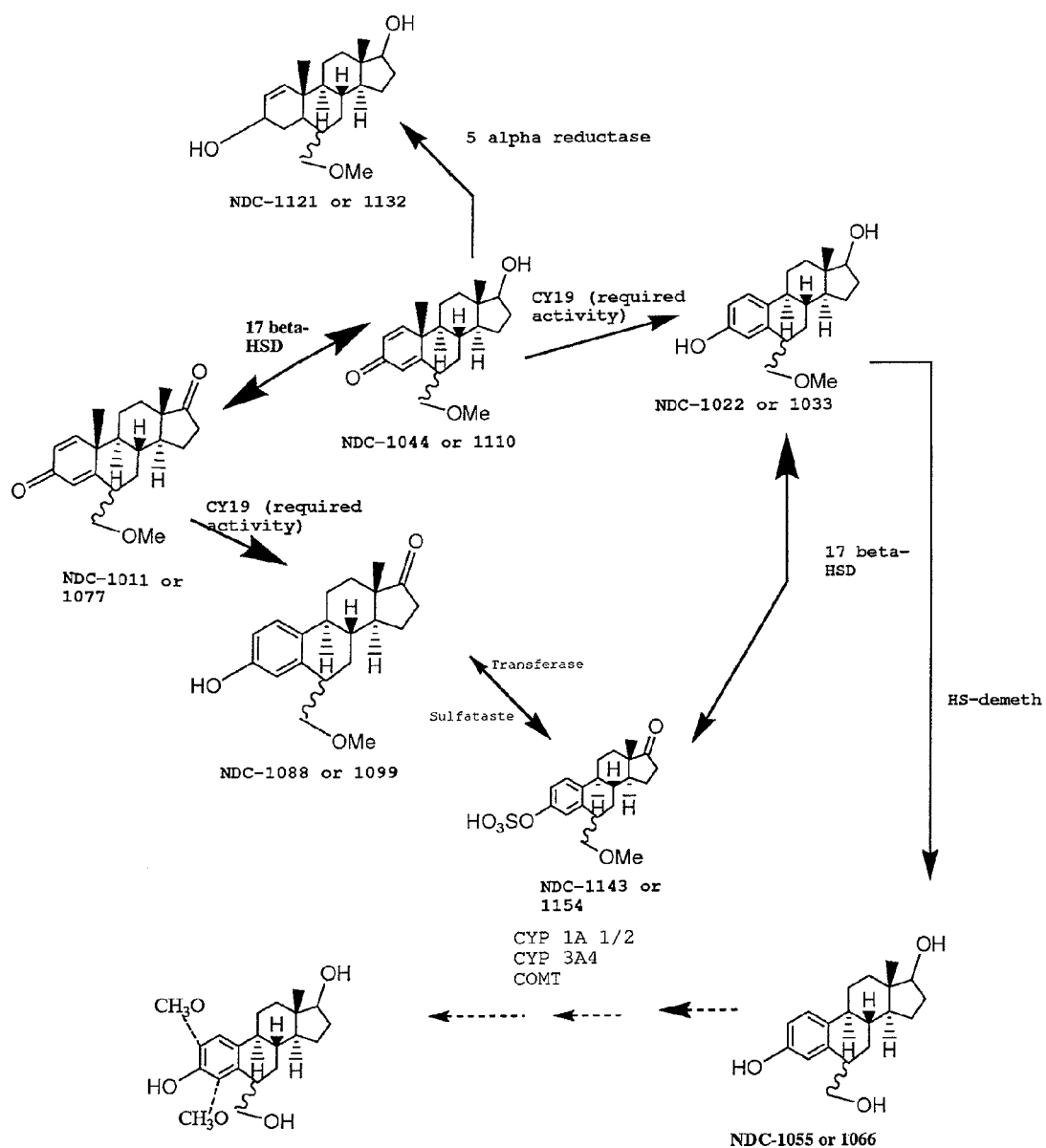

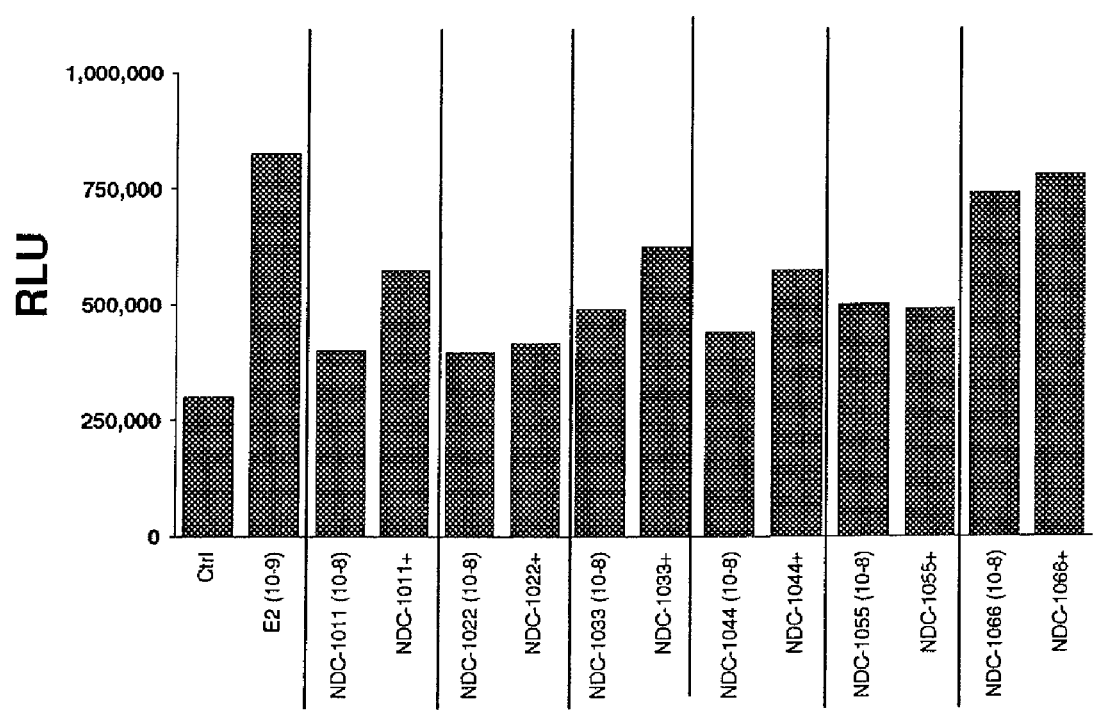
Figure 3. ER beta + ERE

Figure 4: ER alpha + ERE
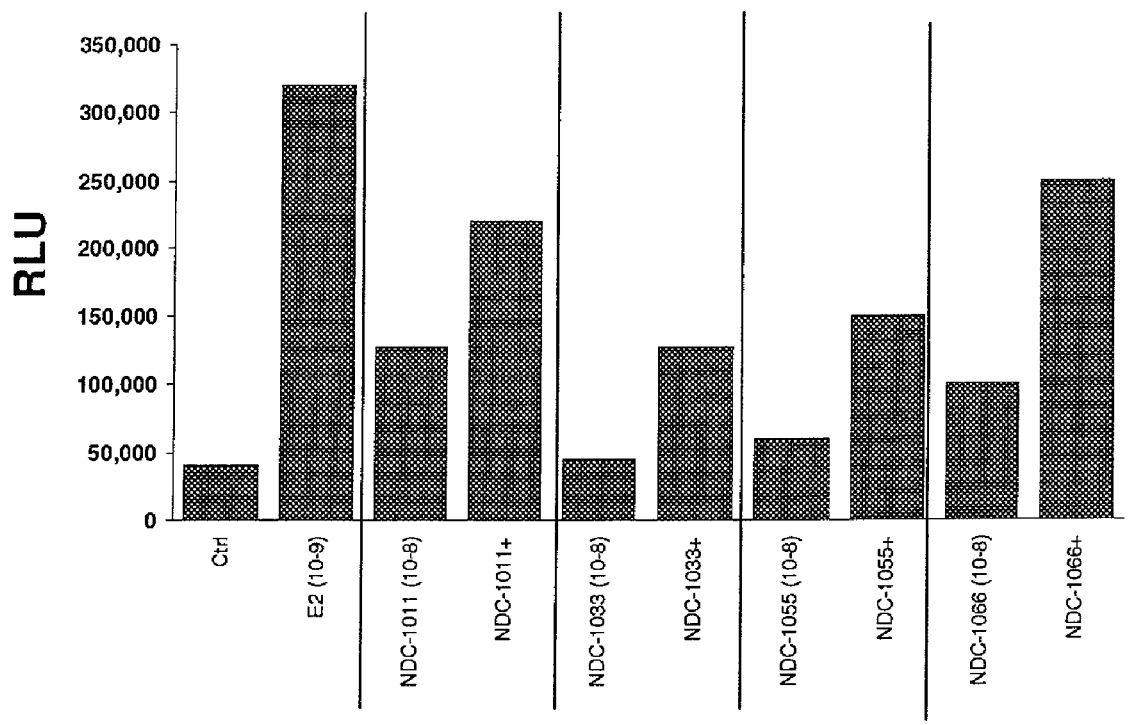

Figure 5: IC50 Data Summary for NDC-1022, NDC-1033 and NDC-1044
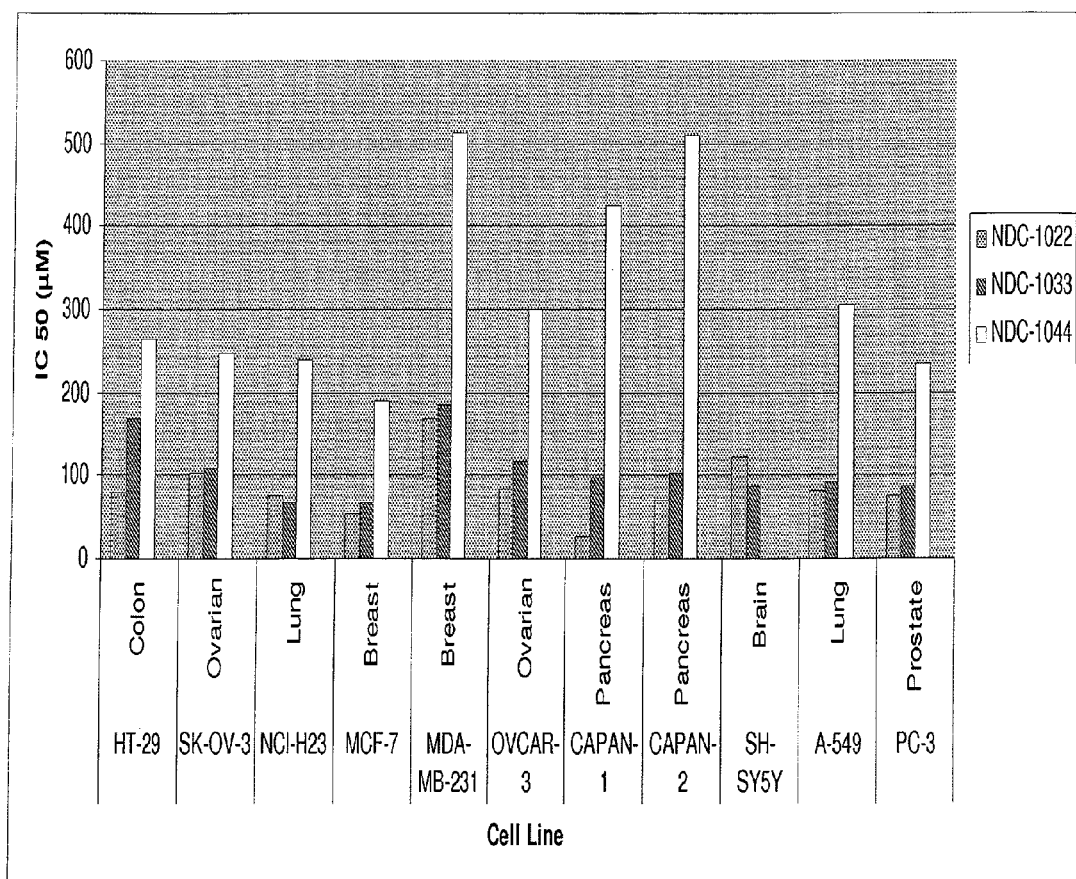

Figure 6: Numerical IC50 Data Summary for NDC-1022, NDC-1033 and NDC-1044 ($\mu$M)

| Cell Line | Tumor Type | NDC-1022 | NDC-1033 | NDC-1044 |
|---|---|---|---|---|
| HT-29 | Colon | 78.5 | 169.9 | 265.7 |
| SK-OV-3 | Ovarian | 102.8 | 108.1 | 247.9 |
| NCI-H23 | Lung | 75.6 | 67.6 | 239.4 |
| MCF-7 | Breast | 53.5 | 68.5 | 190.1 |
| MDA-MB-231 | Breast | 167.8 | 184.8 | 512.2 |
| OVCAR-3 | Ovarian | 85.8 | 117.4 | 298.8 |
| CAPAN-1 | Pancreas | 26.3 | 98.3 | 425.4 |
| CAPAN-2 | Pancreas | 71.2 | 103.9 | 509.5 |
| SH-SY5Y | Brain | 122.3 | 86.9 | ND |
| A-549 | Lung | 81.3 | 92.0 | 304.7 |
| PC-3 | Prostate | 77.2 | 86.0 | 233.8 |

Figure 7
<u>IC50 Values (uM Concentrations)</u>
| Tumor Lines | Type | Test Compound 1 | Test Compound 2 | Test Compound 3 |
|---|---|---|---|---|
| HT-29 | Colon | 75 | > 1000 | 219 |
| NCI-H23 | Lung | 77 | 112 | 162 |
| A549 | Lung | 81 | > 1000 | 163 |
| MCF-7 | Breast | 56 | 520 | 65 |
| MDA-MB-231 | Breast | 130 | 719 | 219 |
| SKOV-3 | Ovary | 133 | > 1000 | 257 |
| OVCAR-3 | Ovary | 83 | > 1000 | 306 |
| PC-3 | Prostate | 79 | 786 | 180 |
| CAPAN-1 | Pancreas | 28 | > 1000 | 271 |
| CAPAN-2 | Pancreas | 73 | > 1000 | 180 |
| SH-SYSY | Brain | 97 | 235 | 478 |
| U-87-MG | Brain | 99 | 236 | 172 |
| U-118-MG | Brain | 117 | > 1000 | 213 |
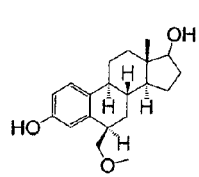    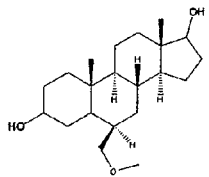    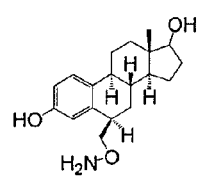
Test Compound 1=NDC-1022    Test Compound 2=NDC-1165    Test Compound 3=NDC 1187

6-SUBSTITUTED ESTRADIOL DERIVATIVES AND METHODS OF USE

CROSS REFERENCE TO RELATED APPLICATIONS

This application is a continuation-in-part of U.S. application Ser. No. 11/947,645 filed on Nov. 29, 2007, currently pending, which claimed the benefit of U.S. Provisional Application No. 60/867,980 filed Nov. 30, 2006, U.S. application Ser. No. 11/947,645 was also a continuation-in-part of U.S. application Ser. No. 11/541,987 filed on Oct. 2, 2006, now U.S. Pat. No. 7,846,918, which claims the priority benefit from U.S. Provisional Application No. 60/722,204 filed Sep. 30, 2005. The teachings of all such applications are incorporated herein by their entirety.

FIELD OF THE INVENTION

The present invention relates to compositions and methods of making and using 6-substituted estradiol compounds including but not limited to 6-alkoxyalkyl estradiol compounds. In particular, the present invention relates to compounds (R or S) 6-hydroxymethyl-, (R or S) methyloxymethyl-, (R or S) 6 methyloxyamine, or 6 aminoalkyl derivatives of (8 R or S, 9S, 13 R or S, 14S, R or S) 13-methyl-7,8,9,11,12,14,15,16,17-decehydrocylopenta [a]phenantherene-3,17-diol and their pharmaceutically acceptable salts, or prodrugs thereof as articulated and described herein. The present invention also pertains to pharmaceutical compositions comprising such compounds, present either in vitro or in vivo, for both diagnostic applications and also treatment of proliferative conditions, such as cancer.

BACKGROUND OF THE INVENTION

Proliferative cell disorders such as tumors and primary malignant tumors {herein, cancer(s)} in particular are problematic given their tendency to invade surrounding tissues and metastasize to distant organs in the body. To date the most frequently used methods for treating neoplasia, especially solid tumor forms of neoplasia, include surgical procedures, radiation therapy, drug chemotherapies, and combinations of the foregoing.

With over million cases of cancer being diagnosed annually, and cancer claiming more than half a million lives in the United States each year, there is increased need in new therapeutic modalities against such condition. Prostate, lung and colorectal remains the most common cancer among men; while breast, colorectal and lung cancers are the most common cancers among women.

In recent years, there have been significant gains in the management of these conditions. At least one of the success stories in the clinical management of a cancer is the early diagnosis and treatment options now available for primary breast cancer. The other is employment of effective and non-toxic anti-estrogen agents that block the actions of estrogen either at its receptor sites or at a point of its synthesis.

Obviously research on the function and activity of estrogen receptors, the structure and their function has been the subject of many recent investigations. Estrogen receptors belong to a large family of structurally related ligand-inducible transcription factors, including steroid receptors, thyroid/retinoid receptors, vitamin D receptors known as nuclear receptors. While the true ligand for nuclear receptors have not been described, there are distinct small molecules that are able to bind to such receptors and trigger a cellular response.

Estrogens and estrogen receptor modulators bind to estrogen receptors, classified into two types; α and β, to form discrete molecular complexes that exert pleiotropic tissue-specific effects by modulating the expression of target genes. The ligand-bound estrogen receptor acts as a key transcription factor in various molecular pathways, and modulation of ER expression levels is important in determining cellular growth potential.

While both these types of receptors bind to estrogen, as well as, other agonists and antagonists, the two receptors have distinctly different localization concentration within the body. Aside from some structural differences between the α and β types, when complexes with estrogen, the two were shown to signal in opposite way, with estrogen activating transcription in the presence of Estrogen Receptor α (ERα) and inhibiting transcription in the presence of Estrogen Receptor β (ERβ).

Tamoxifen is primarily one of the first selective estrogen receptor modulators that have become first-line therapy for hormonal treatment of breast cancer, both for adjuvant treatment and for therapy of metastatic disease. Tamoxifen is a competitive inhibitor of estradiol binding to the estrogen receptor inhibiting its estrogen binding to the estrogen binding element on DNA. It has been suggested that Tamoxifen's binding to the estrogen receptors significantly alters the structural configuration of the estrogen receptors, rendering the binding sites dysfunctional towards any endogenous estrogen. Such structural deformation of the receptor could explain the profound side effect profile associated to the use of Tamoxifen.

At least another shortcoming of Tamoxifen is its ineffectiveness against non-estrogen-dependent tumors and lower efficacy in pre-menopausal women. Additionally, Tamoxifen undergoes an isomerization under physiological conditions from a therapeutically useful antiestrogenic compound to an estrogenic isomer which can stimulate the growth of estrogen-dependent tumor cells, providing an undesired clinical outcome, particularly among patients suffering from estrogen dependent tumors.

U.S. Pat. No. 4,732,904 discloses other type of estrogen receptor antagonists conventionally known as hydrazone compounds. It is thought that these antiestrogenic hydrazone compounds do not undergo isomerization to estrogenic compounds under physiological conditions and the estrogenic side effects observed for Tamoxifen are therefore absent. These hydrazone compounds have been proposed as alternative treatments for estrogen-dependent breast cancers. Among these, the substituted benzophenone nitrophenyl hydrazones, such as 4,4'-dihydroxybenzophenone-2,4-dinitrophenylhydrazone are described to be superior.

The complex of the receptor and the antiestrogen such as hydrazone based compounds or Tamoxifen may then bind to nuclear chromatin in an atypical manner for a longer time than the normal hormone receptor complex. Antiestrogens may also be able to deplete the cytoplasm of free receptor. Either or both of these effects could severely impair the continued growth of an estrogen-dependent tumor.

There has also been an increased interest in the use of aromatase inhibitors to block specifically the local production of estrogens that may contribute substantially to hormone responsive disease such as breast cancer. Aromatase(CYP19) is described as the principal enzyme that converts androgens to estrogens both in pre- and postmenopausal women. Estrogen deprivation through aromatase inhibition is described as an effective and selective treatment for some postmenopausal patients with hormone-dependent breast cancer.

Exemestane (which is sold as Aromasin, is chemically described as 6-methylenandrosta-1,4-diene-3,17-dione) and acts as an irreversible, steroidal aromatase inactivator. It is believed to act as a false substrate for the aromatase enzyme, and processed to an intermediate that binds irreversibly to the active site of the enzyme causing its inactivation. U.S. Pat. Nos. 4,808,616, and 4,904,650, the teachings of which are incorporated herein in their entirety, disclose 6-alkylidenandrosta-1,4-diene-3,17-dione derivatives, such as exemestane, and methods of making them. U.S. Pat. No. 4,876,045 discloses a method of preparing 6-methylene derivatives of androsta-1,4-diene-3,17-diones. U.S. Pat. No. 4,990,635 discloses a process for making 6-methylene derivatives of androsta-1,4-diene-3,17-diones.

The preparation of intermediates that may be useful in preparing exemestane is disclosed in U.S. Pat. No. 3,274,176. In German patent DD 258820, 6-hydroxymethyl-androsta-1,4-diene-3,17-dione is prepared from androsta-1,4-diene-3,17-dione via 1,3-dipyrrolidinoandrosta-3,5-dien-17-one.

Co-pending international application no. PCT/US2005/001248 filed Jan. 14, 2005 (PCT Publication Number WO 2005/070951) also describes the preparation of intermediates that are useful in preparing exemestane, such application is incorporated herein by reference, in its entirety. The structure of Exemestane is shown below.

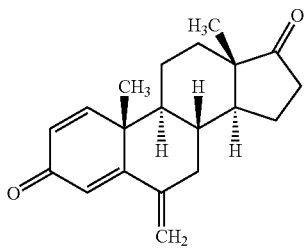

Schneider et. al, in "Course of the reaction of steroidal 3,5-dienamines with formaldehyde", Helvetica Chimica Acta (1973), 56(7), 2396-2404, discloses the following compounds:

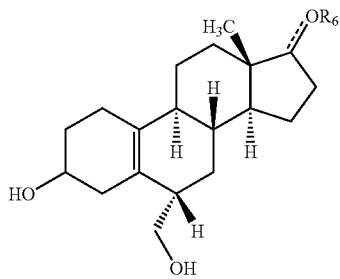

where the ---- symbol represents a double bond, it means a keto group and no $R_6$ is present; and where the ---- symbol represents a single bond $R_6$ is hydrogen (i.e. an alcohol group). Unlike the compounds of the present invention, Schneider's compounds do not embrace estradiol, testostrone or dihydrotestostrone variations.

A tri-hydroxyl substituted derivative of estranes is disclosed in U.S. Pat. No. 3,377,363 to Tadanier et. al, and the 3 hydroxy substituent on the aromatic ring of the present compounds is not disclosed.

U.S. Pat. No. 5,914,324 to De Funari et. al, discloses 6 hydroxy and oxy androstane derivatives for hypertension and heart failure. U.S. Pat. No. 6,384,250 to Gobbini, et al., discloses the hydroxyl and ketone substituents at the 6 position in the preparation of (E,Z) 3-(2-aminoethoxyimino)-androstane-6,17-dione. These compounds were directed towards the treatment of heart failure. The effects of alkyl hydroxyl substitution at the 6 position is not disclosed.

Tanenbaum, et. al, "Crystallographic comparison of the estrogen and progesterone receptor's ligand binding domains", Proc. Natl. Acad. Sci. USA, Biochemistry, Vol. 95, pp 5998-6003, discloses the mechanism of ER receptors and notes that estradiol containing an aromatic ring with a 3-hydroxy substituent binds well with the ER ligand binding region. It is disclosed that a flat aromatic group without the 19 methyl substituent is favored.

U.S. Pat. No. 5,892,069 to D'Amato describes estradiol derivatives that inhibit tubulin polymerization during cell mitosis. Given the above, a need still exists to identify new and effective agents for treating cancer.

Another point of concern in the field is the eventual conversion of some estrogen-dependent cancers, i.e. breast cancer, to estrogen-independent types. This may be accounted for by a natural loss of differentiation by the tumor cells. Estrogen-dependent cancer cells have often been observed to eventually lose their ability to produce estrogen-binding protein receptors and degenerate into much more aggressive estrogen-independent life-threatening cancers. Indeed, the use of antiestrogens to treat estrogen-dependent tumors may lead to the clonal selection of estrogen-independent tumor cells and therefore may promote the conversion of an estrogen-dependent cancer to a non-estrogen-dependent cancer.

Cancers of other organs, such as lung and colon, may not concern estrogen-binding protein receptors and thus are considered independent of estrogens for cell replication. Such estrogen-independent tumors are not as susceptible to the antiestrogenic properties of drugs such as Tamoxifen, aromatase inhibitors. Thus other chemotherapeutic agents must be used to treat such tumors. Many compounds have been documented to be effective to varying degrees against estrogen-independent tumors.

These compounds are reviewed in many references and typically administered in combination regimen chemotherapy causing substantial side effect to the patients. The underlying principle of using general cytotoxic agents chemotherapy is based upon the observation that malignant tumor cells replicate at a higher rate than normal body cells and are therefore correspondingly more susceptible to these compounds. Similarly, normal tissues that proliferate rapidly (for example, bone marrow and intestinal epithelium) are subject to substantial damage once exposed to these potent cytotoxic drugs, and such toxicity often limits utility.

On the other hand, slow growing tumors with a small growth fraction, for example carcinomas of the colon or lung, are often unresponsive to cytotoxic drugs. Aside from the treatment of estrogen-dependent and estrogen-independent tumors, many of the cytotoxic drugs are currently being used for other proliferative diseases with rapidly growing cells involved non-cancerous or non-malignant hyperproliferative conditions.

Also the increasing importance of effective therapeutic management of viral diseases such as AIDS, herpes, various types of hepatitis and bacterial infections, especially among immune suppressed patients, calls for alternative modes of therapy with favorable side effect profile.

Accordingly, there is not only a need for new and improved cancer chemotherapeuty that can be used to treat both estrogen-dependent and estrogen-independent tumors with minimal risk of systemic toxicity challenging the quality of life for such fragile population of patients, but also for therapeutic remedies that target non-cancerous hyperproliferative conditions which can benefit from effective doses of estradiol derivatives. The hyperproliferative cells can be normal, rapidly growing cells or abnormal cells and can include tissue having rapidly growing endogenous cells or their abnormal subpopulation, or other tissues generally exogenous to the patient.

None of the teachings of prior art provide for a therapeutic estradiol derivative with favorable side effect profile that can be used for these types of conditions.

SUMMARY OF THE INVENTION

In light of the foregoing, the present invention is directed towards chemotherapeutic compounds, compositions and methods for their use and preparation, thereby overcoming various deficiencies and shortcomings of the prior art, including those outlined above. Accordingly, it is one object of the present invention to provide compounds useful in the treatment of estrogen-dependent conditions and tumors which provide a better patient tolerance, prognosis and compliance.

Another object of the present invention is to provide compounds and methods for the treatment of estrogen-independent tumors with compounds having substantially less side effects than those currently available to the patients.

Yet another objective of the present invention is to provide for compounds and alternative modes of treatment of tissues afflicted with hyperproliferative conditions, including viral and bacterial infections.

The present invention includes any one of the following sets of compounds represented in Formulas I-XX. One aspect of the present invention pertains to a compound of Formula (I) and (II).

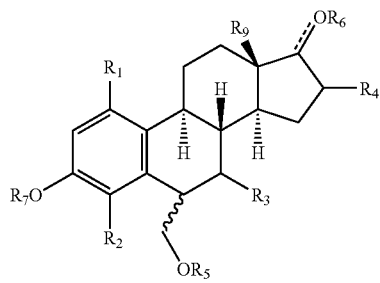

Formula (I)

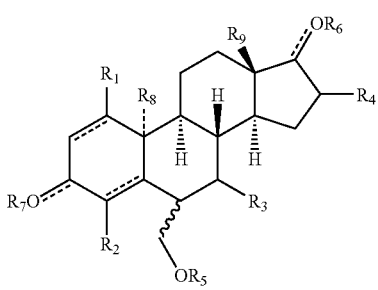

Formula (II)

wherein $R_1$, $R_2$, $R_3$, $R_4$, $R_5$, $R_6$, $R_7$, $R_8$ and $R_9$ are independently selected from the group consisting of hydrogen, $C_1$ to $C_6$ alkyl or substituted alkyl, halogen, sulfate, or glucuronide moieties; and the ≕ symbol represents either a single or a double bond and when the ≕ symbol is a double bond and forms a keto group at position 3 or 17, then no $R_7$ or $R_6$ is present, respectively; the symbol − − − represent the presence or absence of a bond at position 10; and the ⁓ symbol represents any type of bond regardless of the stereochemistry. The compounds also embrace the enantiomers, other stereochemical isomers, hydrates, solvates, tautomers and pharmaceutically acceptable salts thereof.

The present invention relates to a method of therapeutically treating cancer in a mammalian subject (e.g., a human patient). In this aspect of the invention, methods are provided for inhibiting tumor or cancerous cell growth within the mammalian subject. In such a method, the cells are exposed to or contacted with a compound of Formula (I) or (II) or pharmaceutically acceptable enantiomers, other stereochemical isomers, hydrates, solvates, tautomers, or salts thereof, as shown herein. In a specific, non-limiting embodiment of the methods of the present invention, a compound of Formula (I) or (II) is used to therapeutically treat an identified cancer state as described herein. In another specific non-limiting embodiment of the methods of the present invention, a composition comprising a compound of Formula (I) or (II) is used to therapeutically treat an identified cancer state as described herein.

In another aspect of this invention, compounds having Formula (III) and (VIII) are described. In this aspect of the invention, inventor describes methods of inhibiting growth of cancer cells comprising providing to a patient a prodrug of Formula (III) wherein $R_5$ is a methyl or hydrogen;

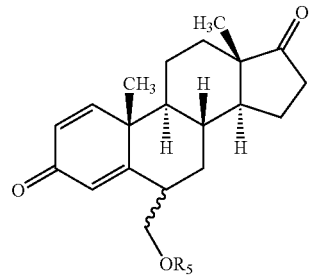

Formula (III)

and forming metabolites having Formulas (IV), (V), (VI), (VII), and (VIII) wherein any of $R_3$, $R_4$, $R_5$, $R_7$, $R_8$ of their Formula II counterparts may be a methyl or a hydrogen. Such metabolites could include for example the structures shown below:

(IV) A - NDC-1088

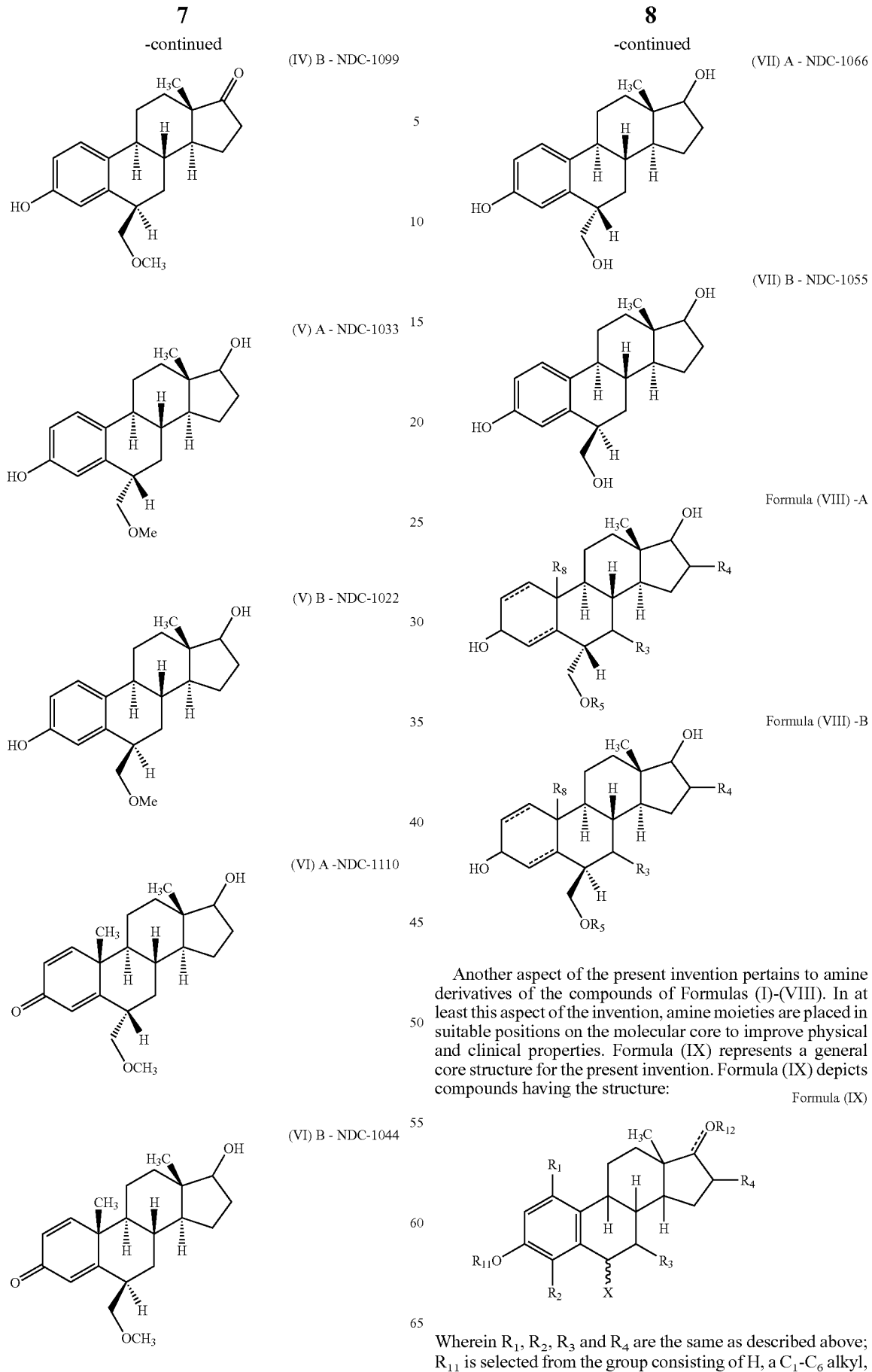

Another aspect of the present invention pertains to amine derivatives of the compounds of Formulas (I)-(VIII). In at least this aspect of the invention, amine moieties are placed in suitable positions on the molecular core to improve physical and clinical properties. Formula (IX) represents a general core structure for the present invention. Formula (IX) depicts compounds having the structure:

Wherein $R_1$, $R_2$, $R_3$ and $R_4$ are the same as described above; $R_{11}$ is selected from the group consisting of H, a $C_1$-$C_6$ alkyl, substituted alkyl, a halogen, a halogenated alkyl, a sulfate, a glucoronide, —SO$_2$NH$_2$, —COOH, —CN, —CH$_2$CN—, —NHCN—, —CHO, =CHOCH$_3$, —COO salt, —OSO$_2$alkyl, —NH$_2$, and —NHCO(CH$_2$)$_n$; R$_{12}$ is selected from a group consisting of H, a C$_1$-C$_6$ alkyl, a substituted alkyl, a sulfate a glucoronide, a bulky group, a phenyl or a substituted phenyl group, a cyclo- or heterocyclo group, and X is selected from the group consisting of: C$_1$-C$_6$ alkyl, a substituted alkyl, a halogen, a halogenated alkyl, a glucoronide, —NH$_2$, —SO$_2$NH$_2$, —COOH, —CN, —CH$_2$CN, —NHCN, —CHO, —COOsalt, —OSO$_2$alkyl, —SH, —SCH$_3$—CH(CH$_2$)nCOOCH$_3$, —(CH$_2$)$_n$—O—CH$_3$, (CH$_2$)$_n$—S—CH$_3$, —CH$_2$OH, —(CH$_2$)$_n$—O—NH$_2$, —(CH$_2$)$_n$—S—NH$_2$, —NH(CH$_2$)$_n$CH$_3$, NH(CH$_2$)$_n$OCH$_3$, —NH(CH$_2$)$_n$CHOH—COOH, —N(CH$_3$)$_2$, —(CH$_2$)$_n$(NH)CH$_2$OH, —NHCOOH, —(CH$_2$)$_n$NHCOOH, —NO$_2$, —SCN, —SO alkyl, —B(OH)$_2$, —(CH$_2$)$_n$N(CH$_3$)—SO$_2$—NH$_3$, —(CH$_2$)$_n$NH—SO$_2$—NH$_2$, —NHC(=S)CH$_3$, and —NHNH$_2$; wherein n is an integer and can be any number between 0-7, the ---- symbol represents either a single or a double bond capable of forming a keto group at position 3 or 17; and the ~ symbol represents any type of bond regardless of the stereochemistry; and the respective enantiomers, other stereochemical isomers, hydrates, solvates, tautomers and pharmaceutically acceptable salts of said compounds.

Another aspect of this invention, concerns the making and using of the following compounds represented by Formula (X)-(XVI):

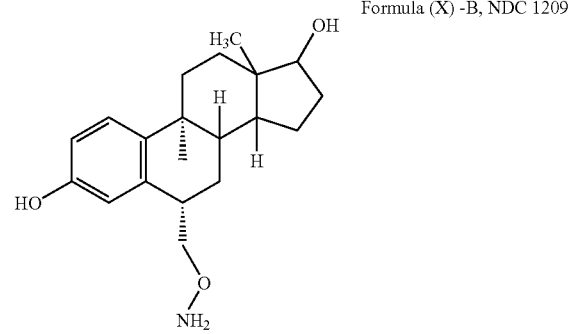

Formula (X) -A, NDC 1187

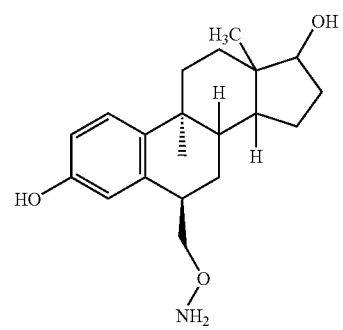

Formula (X) -B, NDC 1209

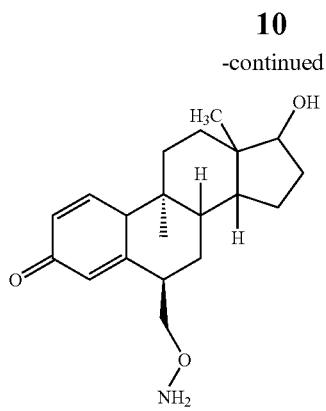

Formula (XI) -A, NDC 1220

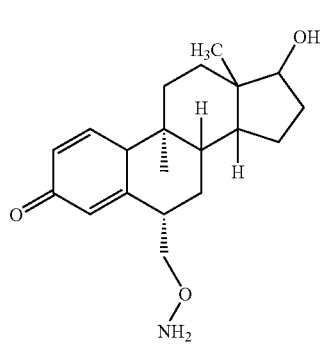

Formula (XI) -B, NDC 1231

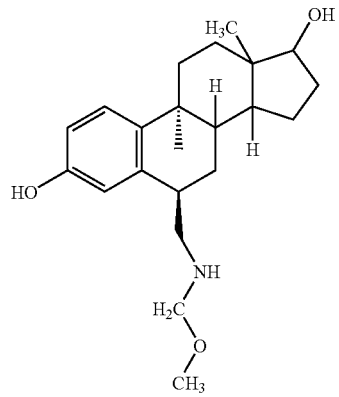

Formula (XII) -A, NDC 1242

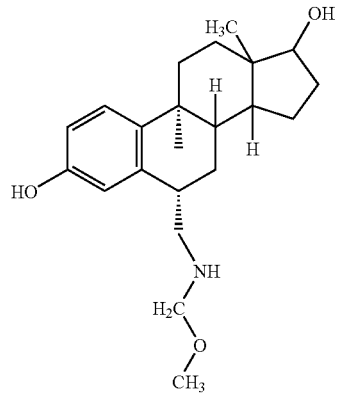

Formula (XII) -B, NDC 1253

-continued

Formula (XIII) -A, NDC 1264

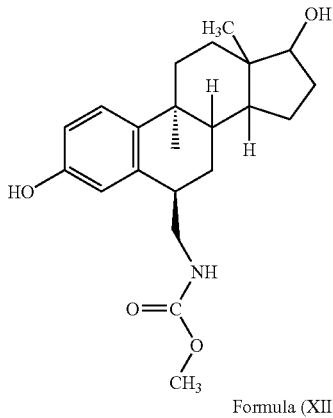

Formula (XIII) -B, NDC 1275

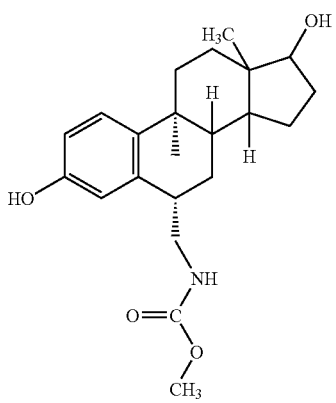

In this aspect of the inventions, the compounds of the present invention may be contemplated for administration to the mammalian subject in the form of a drug, prodrug or even active metabolite. However, it is envisioned that such compounds are most effective when incorporated into nanoparticles, liposomes or polymeric matrix systems or other delivery systems which are capable of being directly delivered to a solid mass or be targeted to tissues of interest via suitable targeting agents.

At least another aspect of the invention concerns delivery systems that allows conversion of suitable analogues which can be converted to a specified active compound in vivo after it is administered to the patient for exerting its therapeutic activity.

The compounds of the present invention may be used to treat any tumor which may be either directly or indirectly effected by hormonal and/or estrogen-related activity, including but not in any way limited to solid tumors associated with breast, pancreatic, lung, colon, prostate, ovarian cancers, as well as brain, liver, spleen, kidney, lymph node, small intestine, blood cells, bone, stomach, endometrium, testicular, ovary, central nervous system, skin, head and neck, esophagus, or bone marrow cancer; as well as hematological cancers, such as leukemia, acute promyelocytic leukemia, lymphoma, multiple myeloma, myelodysplasia, myeloproliferative disease, or refractory anemia.

The compounds of the present invention may also be used in combination-based therapeutic cancer treatments in a mammalian subject. Such methods may comprise administration of a compound of Formula (I), (II), (X), or (XI) in combination with other adjunct cancer therapies, such as chemotherapy, radiotherapy, gene therapy, hormone therapy and other cancer therapies known in the art.

Any of the compounds of the present invention may be contemplated for administration to the mammalian subject in the form of a drug, prodrug or even active metabolite. In the methods of treatment of the present invention, the term "administering" shall encompass the treatment of the various conditions described with the compound specifically disclosed or with a compound which may not be specifically disclosed, but which converts to the specified compound in vivo after administration to the patient and exhibits therapeutic activity.

Other objects, features, benefits and advantages of the present invention will be apparent from this summary and the following descriptions of certain embodiments, and will be readily apparent to those skilled in the art having knowledge of various chemotherapeutic compounds, methods and/or modes of operation.

BRIEF DESCRIPTION OF THE DRAWINGS

FIG. 1—shows the Estradiol biosynthetic pathway.

FIG. 2—shows a predicted metabolic pathway for the present compounds.

FIG. 3—shows the effect of NDC-1011, NDC-1022, NDC-1033, NDC-1044, NDC-1055 and NDC-1066 on estrogen receptor beta (ER-β) activity as measured by luciferase expression (RLU=relative light units). CV-1 cells were transfected with two plasmid constructs, the reporter construct ERE-tk-luciferase and a CMV-ER-β construct. Transfected control (Ctrl) CV-1 cells received no treatment while estradiol treated cells (E2) received estradiol added alone at $10^{-9}$ M (1 nM). In the case of NDC compounds, each compound respectively was either added alone at $10^{-8}$ M (10 nM) (as evident in the left column for each test compound) or at $10^{-8}$ M plus $10^{-9}$ M estradiol (E2) (as evident in the right column for each test compound).

FIG. 4—shows the effect of NDC-1011, NDC-1033, NDC-1055 and NDC-1066 on estrogen receptor alpha (ER-α) activity as measured by luciferase expression (RLU=relative light units). CV-1 cells were transfected with two plasmid constructs, the reporter construct ERE-tk-luciferase and a CMV-ER-α construct. Transfected control (Ctrl) CV-1 cells received no treatment while estradiol (E2) was added alone at $10^{-9}$ M (1 nM). In the case of NDC compounds, each compound respectively was either added alone at $10^{-8}$ M (10 nM) (as evident in the left column for each test compound) or at $10^{-8}$ M plus $10^{-9}$ M estradiol (E2) (as evident in the right column for each test compound).

FIG. 5—shows $IC_H$ growth inhibition data (in μM) for NDC-1022 (left columns), NDC-1033 (middle columns) and NDC-1044 (right columns) as determined in each of the cell lines HT-29, SK-OV-3, NCI-H23, MCF-7, MDA-MB-231, OVCAR-3, CAPAN-1, CAPAN-2, SH-SY5Y, A-549 and PC-3.

FIG. 6—shows numerical $IC_H$ growth inhibition data (in μM) for NDC-1022, NDC-1033 and NDC-1044 as determined in each of the cell lines HT-29, SK-OV-3, NCI-H23, MCF-7, MDA-MB-231, OVCAR-3, CAPAN-1, CAPAN-2, SH-SY5Y, A-549 and PC-3.

FIG. 7—shows numerical $IC_{50}$ growth inhibition data (in μM) for Compound 1 (NDC-1022), Compound 2 (NDC-1165) and Compound 3 (NDC-1187) as determined in each of the cell lines HT-29, SK-OV-3, NCI-H23, MCF-7, MDA-MB-231, OVCAR-3, CAPAN-1, CAPAN-2, SH-SY5Y, A-549, PC-3, U-87-MG and U-118-MG.

DETAILED DESCRIPTION OF THE INVENTION

Figure 8:
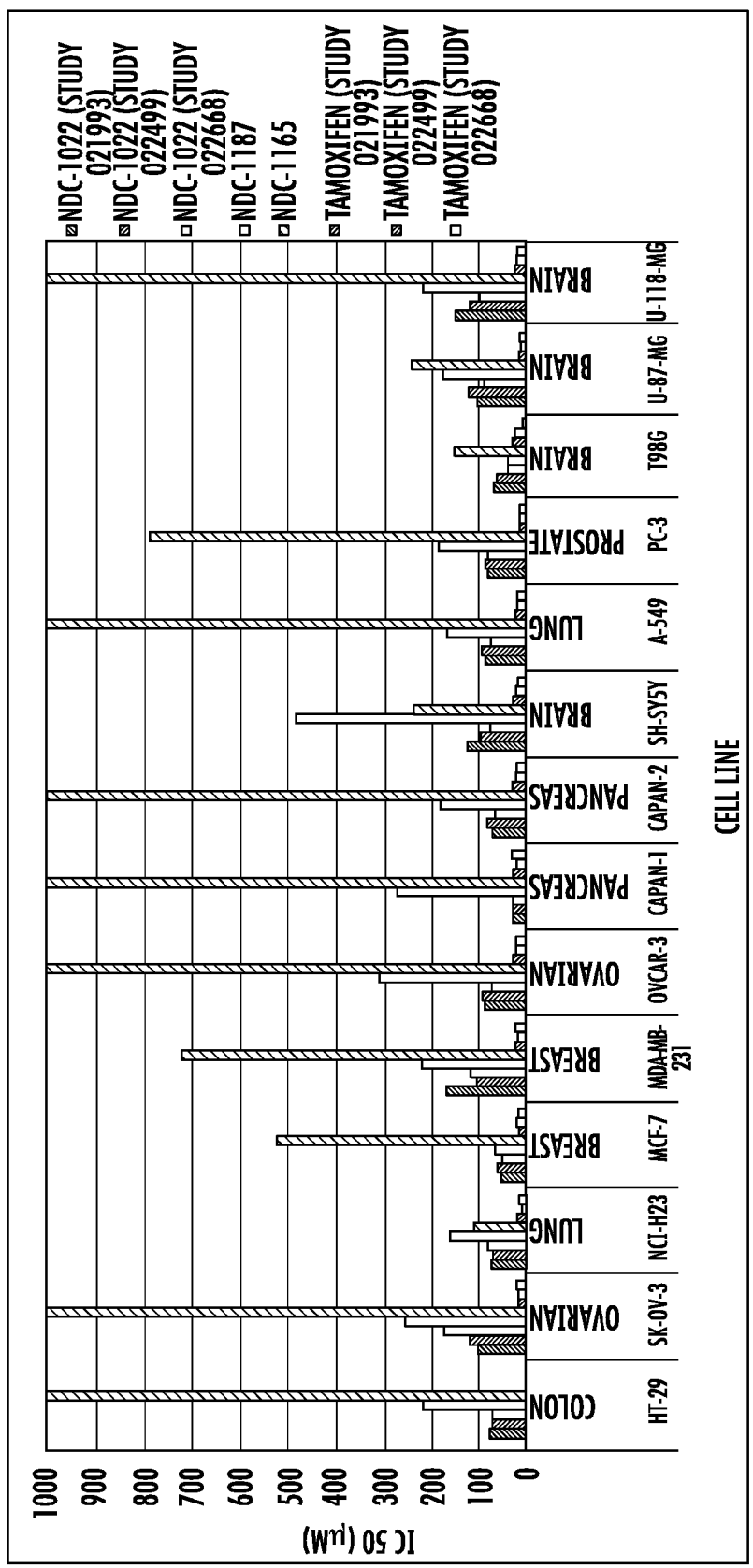
FIG. 8—shows $IC_{50}$ growth inhibition data (in μM) for NDC-1022 (three left columns), NDC-1187 (fourth columns from left), NDC-1165 (fifth columns from left), and tamoxifen controls (three right columns) as determined in each of the cell lines HT-29, SK-OV-3, NCI-H23, MCF-7, MDA-MB-231, OVCAR-3, CAPAN-1, CAPAN-2, SH-SY5Y, A-549, PC-3, T98G, U-87-MG and U-118-MG.

Unless defined otherwise, all technical and scientific terms used herein have the same meaning as is commonly understood by one of skill in the art to which this invention belongs and shall be understood to have the meanings described below. All publications and patents referred to herein are incorporated by reference in their entirety. Unless otherwise specified, a reference to a particular compound includes all such isomeric forms, including racemic and other mixtures thereof. Unless otherwise specified, a reference to a particular compound also includes ionic, salt, solvate (e.g., hydrate), protected forms, prodrugs, and other stereoisomers thereof, for example, as discussed herein.

It may be convenient or desirable to prepare, purify, and/or handle a corresponding salt of the active compound, for example, a pharmaceutically-acceptable salt. Examples of pharmaceutically acceptable salts are discussed in Berge et al., 1977, "Pharmaceutically Acceptable Salts," J. Pharm. Sci., Vol. 66, pp. 1-19, and discussed herein.

Anti-proliferative compounds of the present invention have application in the treatment of cancer, and so the present invention further provides anti-cancer agents. The term "anti-cancer agent" as used herein, pertains to a compound which treats, delays progression, prolongs relapse period of, and controls symptoms of a cancer (i.e., a compound which is useful in the treatment of a cancer). The anti-cancer effect may arise through one or more mechanisms, including but not limited to, the regulation of cell proliferation, the inhibition of angiogenesis (the formation of new blood vessels), the inhibition of metastasis (the spread of a tumor from its origin), the inhibition of invasion (the spread of tumor cells into neighboring normal structures), or the promotion of apoptosis (programmed cell death), or tumor necrosis or tumor autophagy or any combinations thereof.

The invention further provides active compounds for use in a method of treatment of the human or animal body by therapy. Such a method may comprise administering to such a subject a therapeutically-effective amount of an active compound, preferably in the form of a pharmaceutical composition as discussed further herein.

The term "estrogen" as used herein encompass steroid like hormones that are naturally made and is able to cross the cell membrane to exert its activity inside the cell by binding to the estrogen receptors. Example of such compounds include but are not limited to estradiols, estrols, and esterenes.

The term "treatment," or "therapy" as used herein in the context of treating a condition, pertains generally to treatment and therapy of a mammalian subject, whether of a human or a non-human animal (e.g., in veterinary applications), in which some desired therapeutic effect is achieved, for example, the inhibition of the progress of the condition, and includes a reduction in the rate of progress, a halt in the rate of progress, amelioration of the condition, and/or cure of the condition. Treatment as a prophylactic measure is also included. Treatment includes combination treatments and therapies, in which two or more treatments or therapies are combined, for example, sequentially or simultaneously. Examples of treatments and therapies include, but are not limited to, chemotherapy (the administration of active agents, including, e.g., drugs, antibodies (e.g., as in immunotherapy), prodrugs (e.g., employing protecting groups including phosphoric acid derivatives and phosphinates at suitable positions such as position 3 or 17, other compounds used for photodynamic therapy, GDEPT, ADEPT, etc.); surgery; radiation therapy; and gene therapy.

The term "stereochemical isomer" as used herein, refers to isomers that differ from each other only in the way the atoms are oriented in space. The two stereoisomers particularly of importance in the instant invention are enantiomers and diastereomers depending on whether or not the two isomers are mirror images of each other. In the preferred embodiment, the claimed formulations comprise such compounds that isolated, resolved and are "substantially free of other isomers."

The term "therapeutically-effective amount," as used herein, pertains to that amount of an active compound, or a material, composition or dosage form comprising an active compound, which is effective for producing some desired therapeutic effect, commensurate with a reasonable benefit/risk ratio.

The term "patient" refers to animals, including mammals, preferably humans.

The term "region of a patient" refers to a particular area or portion of the patient afflicted with a proliferative disorder, cancer or tumor and in some instances to regions throughout the entire patient. Exemplary of such regions are the pulmonary region, the gastrointestinal region, the breast region, the renal region as well as other bodily regions, tissues, lymphocytes, receptors, organs and the like, including the vasculature and circulatory system, and cancerous tissue. "Region of a patient" includes, for example, regions to be treated with the disclosed compounds and compositions. The "region of a patient" is preferably internal, although it may be external.

The term "tissue" refers generally to specialized cells which may perform a particular function. The term "tissue" may refer to an individual cell or a plurality or aggregate of cells, for example, membranes, blood or organs. The term "tissue" also includes reference to an abnormal cell or a plurality of abnormal cells. Exemplary tissues include breast tissue, including breast cells, membranous tissues, including endothelium and epithelium, laminae, connective tissue, including interstitial tissue, and tumors.

The term "amino alkyl" as used herein refers to an alkyl group with an amino group on it, for example, H2N—CH2-, H2N—CH2CH2-, Me2NCH2-, etc., wherein the point of attachment is a carbon of the alkyl chain; and the term "alkyl amino" as used herein refers to an amino group with an alkyl group attached to the nitrogen atom, for example, CH3NH—, EtNH—, iPr-NH—, etc., wherein the point of attachment is via the nitrogen atom of the amino group.

The term "proliferative cell disorders" as used herein refers to disorders such as tumors, primary malignant tumors, and other hyperproliferative conditions. The terms "primary malignant tumor(s)" and "cancer(s)" are used interchangeably.

Compounds

Among other things, the present invention relates to estradiol derivatives with specific modifications at position 6 of the B ring of the estradiol. At least one aspect of this invention is directed to such compounds having the general structure shown in Formula (IX) below:

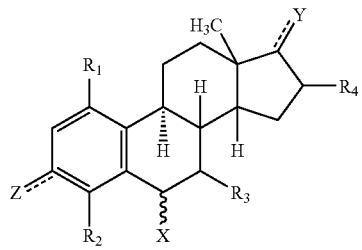

wherein $R_1$, $R_2$ and Z are independently selected from the group consisting of: H, $C_1$-$C_6$ alkyl, substituted alkyl, a halogen, a halogenated alkyl, a sulfate, a glucoronide, —$SO_2NH_2$, —COOH, —CN, —$CH_2CN$, —NHCN, —CHO, —COOsalt, —$OSO_2$alkyl, —$NH_2$, —SH, —$SCH_3$, —$NHCO(CH_2)_n$$CH_3$, —$NO_2$, —SCN, —SO alkyl, —$B(OH)_2$, —NHC(=S) $CH_3$, and —$NHNH_2$; X is selected from the group consisting of: $C_1$-$C_6$ alkyl, a substituted alkyl, a halogen, a halogenated alkyl, a glucoronide, —$NH_2$; —$SO_2NH_2$, —COOH, —CN, —$CH_2CN$, —NHCN, —CHO, —COOsalt, —$OSO_2$alkyl, —SH, —$SCH_3$—$CH(CH_2)_n$ $COOCH_3$, —$(CH_2)_n$—O—$CH_3$, —$(CH_2)_n$—S—$CH_3$, —$CH_2OH$, —$(CH_2)_n$—O—$NH_2$; —$(CH_2)_n$—S—$NH_2$, —$NH(CH_2)_nCH_3$, —$NH(CH_2)_n$$OCH_3$, —$NH(CH_2)_nSCH_3$—$NH(CH_2)_nCHOH$—COOH, —$N(CH_3)_2$, —$(CH_2)_n(NH)CH_2OH$, —NHCOOH, —$(CH_2)_n$NH—COOH, —$NO_2$, —SCN, —SO alkyl, —$B(OH)_2$, —$(CH_2)_nN(CH_3)$—$SO_2$—$NH_3$, —$(CH_2)_n$NH—$SO_2$—$NH_2$, —NHC(=S)$CH_3$, and—$NHNH_2$; $R_3$ is selected from the group consisting of: H, a $C_1$-$C_6$ alkyl, a substituted alkyl, a halogen, and a halogenated alkyl; $R_4$ and Y are independently selected from a group consisting of: =O, —OH, —H, a —$C_1$-$C_6$ alkyl, a substituted alkyl, a halogen, a halogenated alkyl, a sulfate, a glucoronide, a bulky group, a phenyl or a substituted phenyl group, a cyclo- or heterocyclo group, piperidine, pypirizine, morpholine, pyrimidine, —$N(CH_2)_n$; a phosphate group, a phosphinate group, and further wherein n is independent integers and can be any number between 0-7, the ---- symbol represents either a single or a double bond capable of forming a keto group at position 3 or 17; and the ~ symbol represents any type of bond regardless of the stereochemistry; and the respective enantiomers, other stereochemical isomers, hydrates, solvates, tautomers and pharmaceutically acceptable salts of said compounds. In an another embodiment the stereochemistry at the C-6 carbon comprises a S or R enantiomer or diastereomers.

In at least another aspect of the present invention, preferred compounds having the general structure shown in Formula (XIX) below:

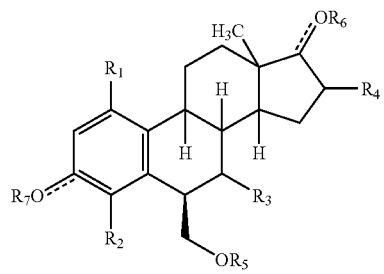

wherein:
$R_1$, $R_2$, $R_3$, $R_4$ are independently selected from the group consisting of H, $C_1$-$C_6$ alkyl, substituted alkyl, and halogen;

$R_5$ is selected from the group consisting of H, $C_1$-$C_6$ alkyl, a substituted alkyl, a sulfate, a glucuronide, —$CH_2OH$, —$CH_2OCH_3$, —$NH(CH_2)_nOH$, —$NH(CH_2)_n$—COOsalt, —$N(CH_3)_n$, —$CH_2ONH_2$, —(NH)$CH_2OHCH_3$, $(CH_2)_n$NH-COOH—$(CH_2)_n$NHCOOsalt, —$NHCH_2OH$, —NHCOOH and —$NH_2$, $R_6$ is selected from a group consisting of H, a $C_1$-$C_6$ alkyl, a substituted alkyl, a sulfate a glucuronide, a bulky group, a phenyl or a substituted phenyl group, a cyclo- or heterocyclo group, and $R_7$ is selected from the group consisting of H, a $C_1$-$C_6$ alkyl, substituted alkyl, a halogen, a halogenated alkyl, a sulfate, a glucuronide, —$SO_2NH_2$, —COOH, —CN, —$CH_2CN$—, —NHCN, —CHO, —COO salt, and —$NH_2$.

In an another embodiment the stereochemistry at the C-6 carbon comprises a S or R enantiomer or diastereomers.

Wherein the ---- symbol represents either a single or a double bond with the proviso that when the ---- symbol is a double bond and forms a keto group at position 3 or 17, then no $R_7$ or $R_6$ is respectively present.

In at least another aspect of the present invention is directed to a chemotherapeutic compound of a Formulas (I)-(II):

Formula (I)

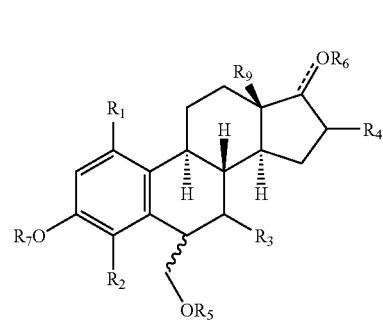

Formula (II)

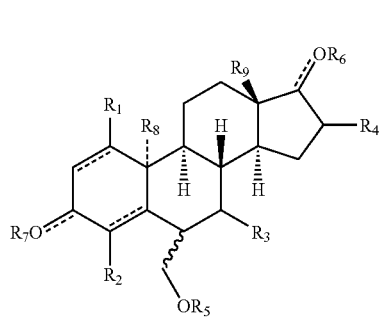

wherein $R_1$, $R_2$, $R_3$, $R_4$, $R_5$, $R_6$, $R_7$, $R_8$ and $R_9$ are independently hydrogen, $C_1$ to $C_6$ alkyl or substituted alkyl, halogen, sulfate, or glucuronide moieties; and the ═══ symbol represents either a single or a double bond and when the ──── symbol is a double bond and forms a keto group at position or 17, then no $R_7$ or $R_6$ is present, respectively; the symbol ··· represent the presence or absence of a bond at position 10; and the ─ symbol represents any type of bond regardless of the stereochemistry. The compounds also embrace the enantiomers, other stereochemical isomers, hydrates, solvates, tautomers and pharmaceutically acceptable salts thereof.

In an embodiment of Formula I, $R_5$, $R_6$, $R_7$, $R_9$ are hydrogen atoms, methyl or Cl; $R_1$, $R_2$ is hydrogen or methyl; $R_3$, $R_4$ is $C_1$ to about $C_6$ alkyl or substituted alkyl, halogen and ═══ is a single bond corresponding to the alcohol group. In an another embodiment the stereochemistry at the C-6 carbon comprises a S or R enantiomer or diastereomers.

Embodiment compounds of the present invention can be used in a pharmaceutical composition. Such a composition can comprise one or more compounds selected from those discussed above, illustrated below or otherwise inferred herein, and combinations thereof. In certain embodiments, such a composition can comprise a pharmaceutically-acceptable carrier component. Without limitation, such a composition can comprise a racemic mixture of compounds. In certain embodiments, such a compound can be present as the S and R enantiomer, preferably their isolated and purified form which is substantially free of other isomers, and $R_5$, or $R_7$ can be selected from H, $C_1$ to $C_6$ alkyl or substituted alkyl, and a halogen.

The compounds of the present invention may have asymmetric centers and may occur as racemate, racemic mixture or as individual and purified diastereomers or enantiomers such as (S)-6-methyloxymethyl(8S,9S,13S,14S, 17S)-13-methyl-7,8,9,11,12,14,15,16,17-decehydrocylopenta [a]phenantherene-3,17-diol; (R) 6-methyloxymethyl(8S,9S, 13S,14S, 17R)-13-methyl-7,8,9,11,12,14,15,16,17-decehydrocylopenta[a]phenantherene-3,17-diol; (R)-6-methyloxymethyl(8R,9S,13R,14S,17R)-13-methyl-7,8,9, 11,12,14,15,16,17-decehydrocylopenta[a]phenantherene-3, 17-diol (NDC-1022); (S)-6-methyloxymethyl(8R,9S,13R, 14S, 17R)-13-methyl-7,8,9,11,12,14,15,16,17-decehydrocylopenta [a]phenantherene-3,17-diol (NDC-1033). (6R,8R,9S,10R, 13S,14S)-6-(methoxymethyl)-10,13-dimethyl-7,8,9,10,11,12,13,14,15,16-decahydro-3 H-cyclopenta [a]phenanthrene-3,17(6H)dione (NDC-1011); (6R,8R,9S,10R, 13S,14S)-17-hydroxy-6-(methoxymethyl)-10,13-dimethyl-6,7,8,9,10,11,12,13,14,15,16,17-dodecahydro-3H-cyclopenta[a]phenanthrene-3-one(NDC-1044); (6R, 8R,9S,13S, 14S)-6-(hydroxymethyl)-13-methyl-7,8,9,11, 12,13,14,15,16,17-decahydro-6H-cyclopenta[a] phenanthrene-3,17-diol (NDC-1055); (6S,8R,9S,13S,14S)-6-(hydroxymethyl)-13-methyl-7,8,9,11,12,13,14,15,16,17-decahydro-6H-cyclopent[a]phenanthrene-3,17-diol(NDC-1066); (6S,8R,9S,10R,13S,14S)-6-(methoxymethyl)-10,13-dimethyl-7,8,9,10,11,12,13,14,15,16-decahydro-3H cyclopenta[a]phenanthrene-3,17(6H)-dione(NDC-1077); (6S,8R, 9S,13S,14S)-3-hydroxy-6-(methoxymethyl)-13-methyl-7,8,9,11,12,13,15,16-octahydro-6H-cyclopenta[a] phenanthren-17(14H)-one(NDC-1088); (6R,8R,9S,13S, 14S)-3-hydroxy-6-(methoxymethyl)-13-methyl-7,8,9,11, 12,13,15,16-octahydro-6H-cyclopenta[a]phenanthren-17 (14H)-one(NDC-1099); (6S,8R,9S, 10R,13S,14S)-17-hydroxy-6-(methoxymethyl)-10,13-dimethyl-6,7,8,9,10,11, 12,13,14, 15, 16,17-dodecahydro-3H-cyclopenta[a] phenanthrene-3,17-diol(NDC-1110); (6R,8R,9S, 10R,13S, 14S)-6-(methoxymethyl)-10, 13, dimethyl-4,5,6,7,8,9,11, 12,13,14,15,16,17-tetradecahydro-3H-cyclopenta[a] phenanthrene-3,17-diol(NDC-1121); (6S,8R,9S, 10R,13S, 14S)-6-(methoxymethyl)-10,13-dimethyl-4,5,6,7,8,9,10,11, 12,13,14,15,16,17-tetradecahydro-3H-cyclopenta[a] phenanthrene-3,17-diol(NDC-1132); (6R,8R, 9S,10R,13S, 14S)-6-(methoxymethyl)10,13-dimethylhexadecahydro-1H-cyclopenta[a]phenanthrene-3,17-diol (NDC-1165); (6R, 8R, 9S,13S,14S)-3-hydroxy-6-(methoxymethyl)-13-methyl-7,8,9,11,12,13,14,15,16,17-decahydro-6H-cyclopenta[a]-17-yl stearate (NDC-1176); (6R,8R,9S,13S,14S)-6-(aminooxymethyl)-13-methyl-7,8,9,11,12,13,14,15,16,17-decahydro-6H-cyclopenta[a]phenanthrene-3,17-diol (NDC-1187); (6R,8R,9S,13S,14S)-6-methoxy-13-methyl-7,8,9,11, 12,13,14,15,16,17-decahydro-6H-cyclopenta[a] phenanthrene-3,17-diol (NDC-1198).

An embodiment of the present invention pertains to the preparation of the R or S enantiomers, R or S diastereomers of 6 substituted estradiols. Methods for the preparation (e.g., asymmetric synthesis) and separation (e.g., fractional crystallization and chromatographic means) of such isomeric forms are either generally known in the art or are readily obtained by adapting the methods taught herein.

One such methodologies are described in the co-pending U.S. application Ser. No. 11/541,987, the teachings of which are herein incorporated in its entirety.

Another embodiment of present invention pertains to a method for preparing a 6-hydroxymethyl, 6-methyloxymethyl, 6-aminomethoxy, 6-methylaminomethoxy or 6-methoxyamine derivatives of estradiol. A reaction scheme for preparing estradiol derivatives is given below, Schemes 1-3. Such methods can comprise reaction of t-butyldimethylsilyl derivative of estradiol with LIDAKOR/THF/formaldehyde to obtain a 6-hydroxylated compound followed by such steps as: (i) hydrolysis to obtain 6-hydroxymethyl derivative of estradiol, NDC-1066; and/or (ii) treatment with dimethylsulfate followed by hydrolysis to obtain 6-methyloxymethyl derivative of estradiol, NDC-1033. NDC-1088 can be obtained by further oxidation of NDC-1033 at the C-17 hydroxyl position.

In an alternative approach, the compounds of the present invention can also be prepared by a method comprising such steps as: (i) protecting an estrodial compound, (ii) acylating the protected estradiol compound at the benzylic 6-position with LIDAKOR/Butyl-Lithium/Diisopropylamine/potassium tert-amylate, (iii) reducing the position 6 aldehyde with lithium aluminum hydride, (iv) deprotecting the protected regions of the estradiol compound. A reaction scheme for preparing estradiol derivatives is given below in Scheme 2.

The compounds of the present invention can be synthesized by the following methods as depicted in the schemes below:

Scheme 1 - Sharing compounds of the instant invention.
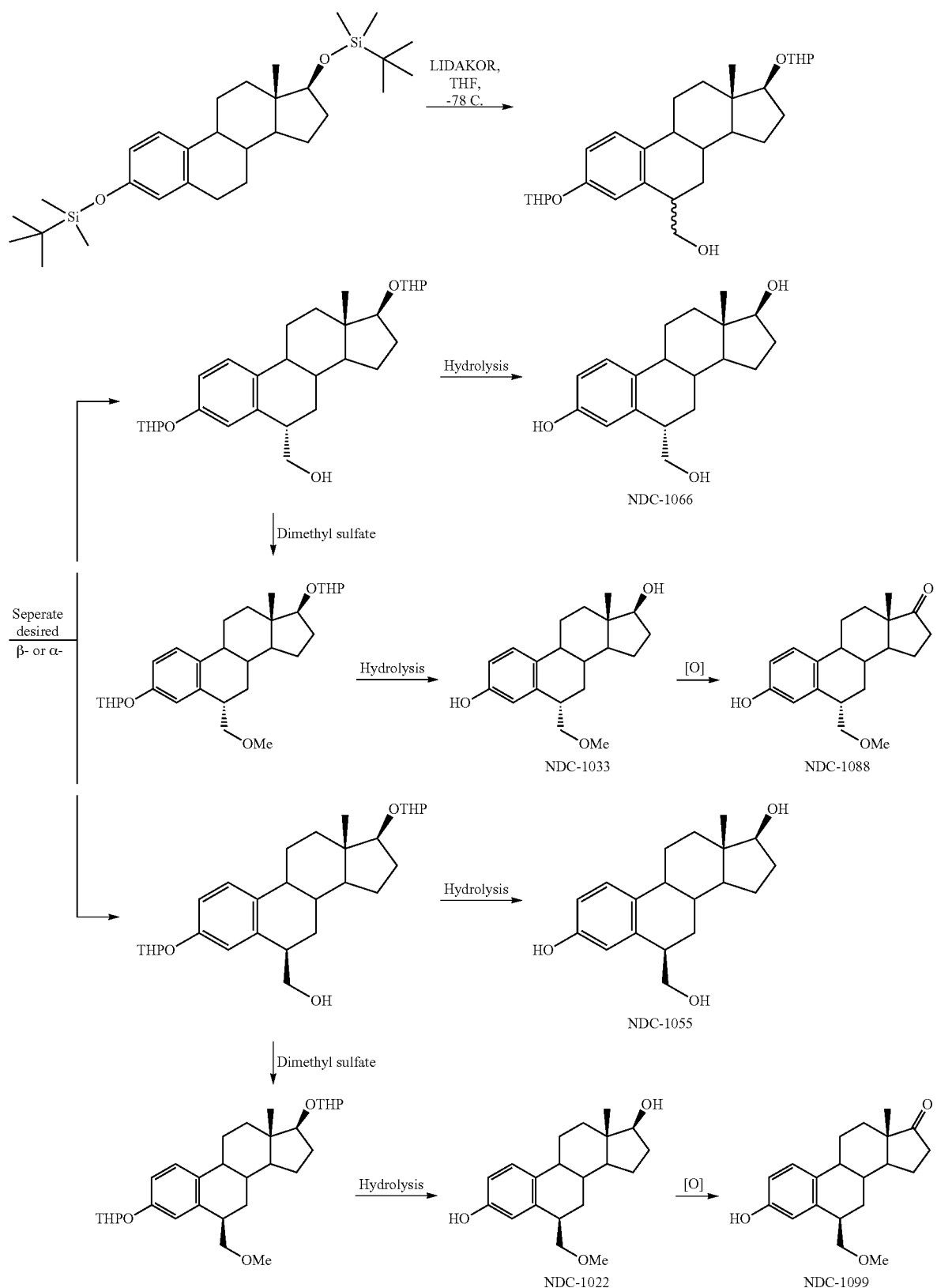

Scheme 2 - Alternative methods for preparing the compounds of the invention.
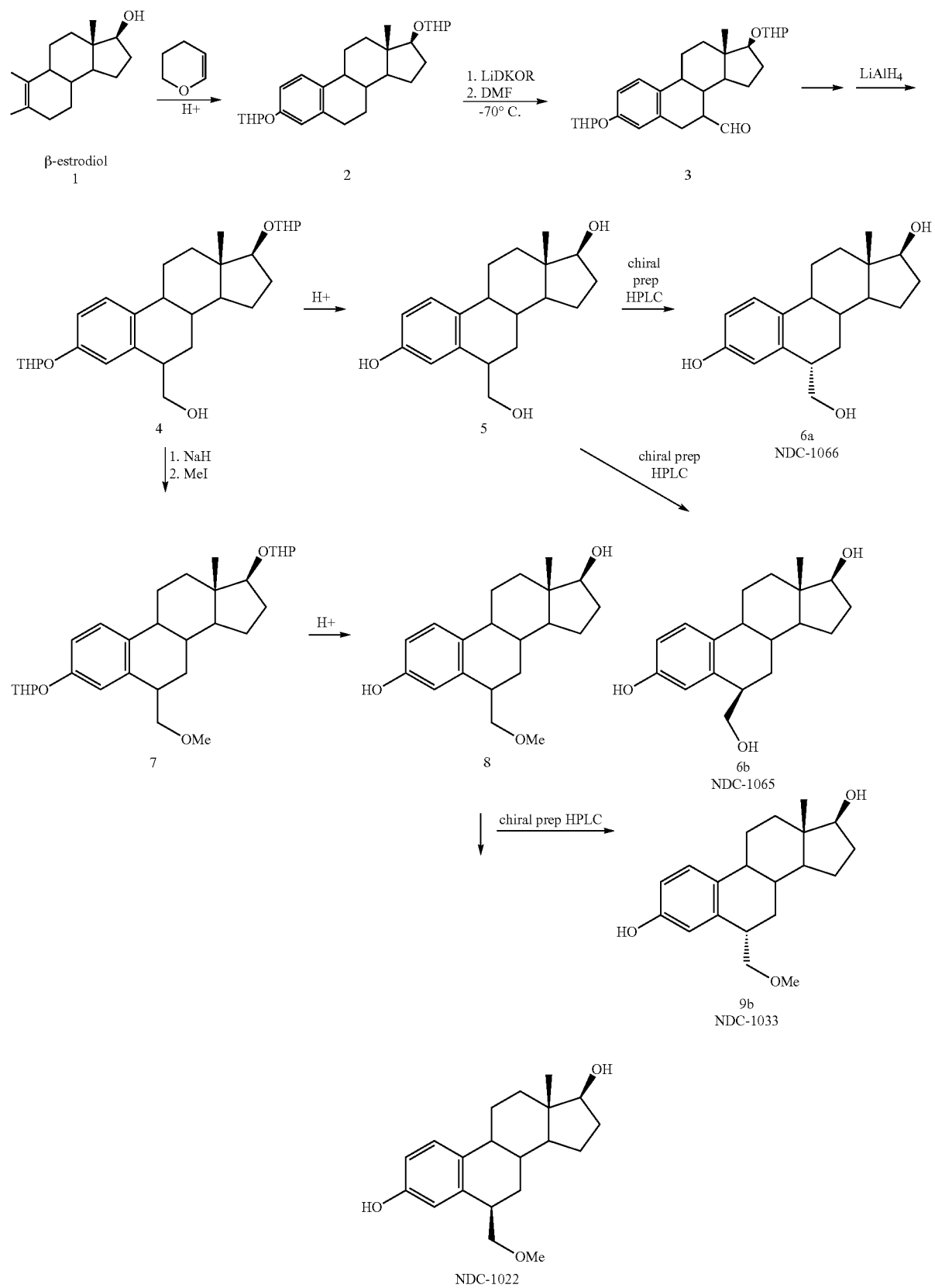

Various methyloxyalkyl derivatives, in accordance with this invention, involve selection of alkylating agents. Such derivatives would be understood by those skilled in art made aware of this invention, and is available through synthetic procedures of the sort described herein. Accordingly, without limitation, various $C_1$ to $C_6$ alkyl and substituted alkyl (e.g., $C_1$ to $C_6$ linear, substituted linear, branched and substituted branched alkyl, such substituents as would be understood in the art) reagents can be used as described herein to prepare the corresponding methyloxyalkyl derivatives.

In another aspect of this invention, methods of making 6-amino derivatives of the estradiol are disclosed in reaction schemes below. Accordingly, 6-methoxylated estradiols described in Schemes 1-2 are employed and converted to their respective amino derivatives.

Scheme 3- Methods of making 6-amino derivatives of estradiol:

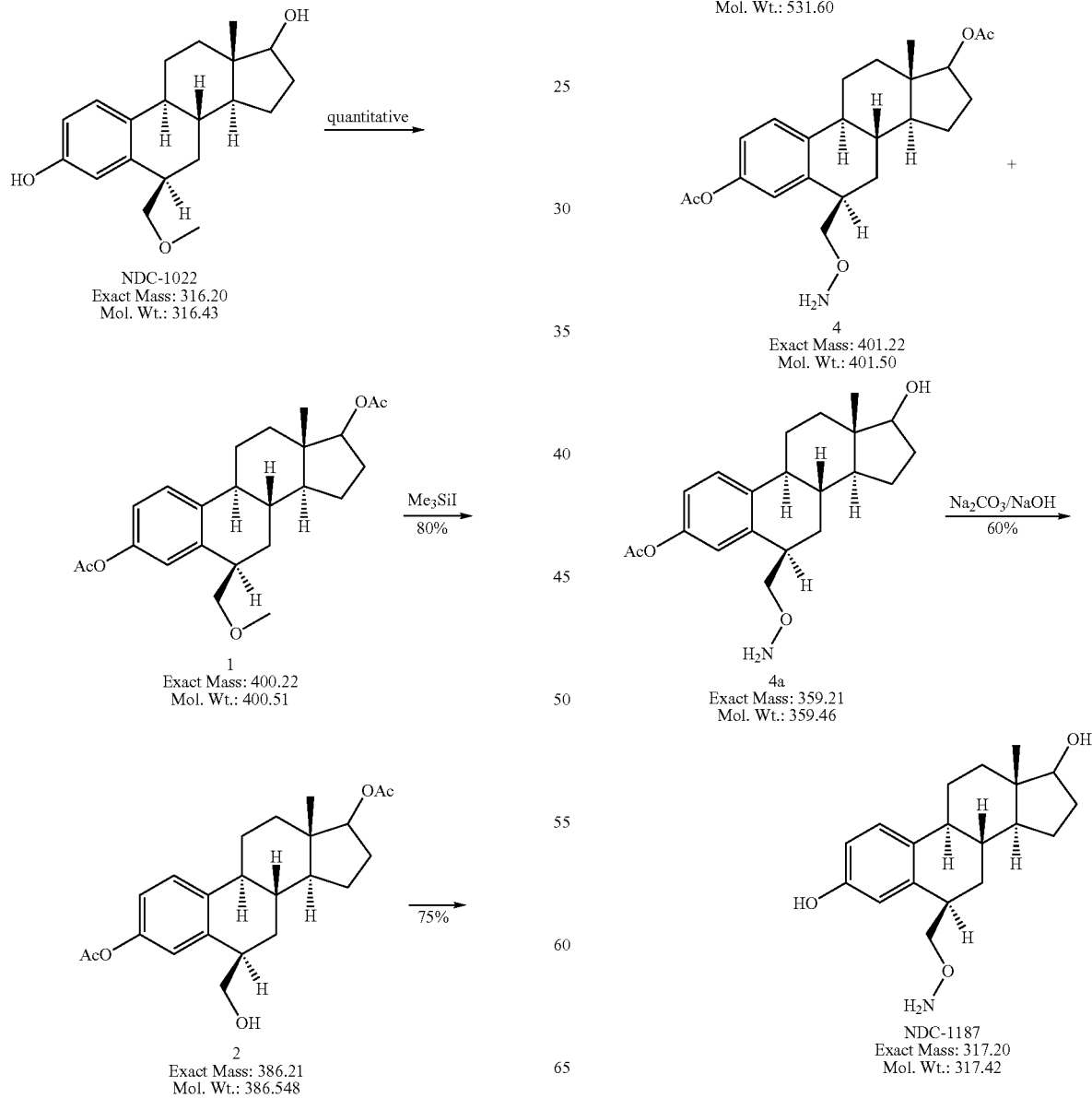

Methods of Use

The present invention relates to a method of treating cancer in a mammalian subject (e.g., a human patient). In this aspect of the invention, methods are provided for inhibiting tumor or cancerous cell growth. In such a method, the cells are exposed to or contacted with a compound of Formula (IX) or pharmaceutically acceptable salts or hydrates thereof having the general structure shown in Formula (IX) below:

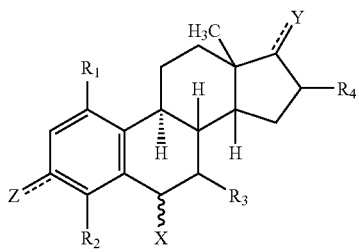

wherein $R_1$, $R_2$, $R_3$, $R_4$, Y, X and Z are as described above, and further wherein n and m are independent integers and can be any number between 0-7, the ---- symbol represents either a single or a double bond capable of forming a keto group at position 3 or 17; and the ~~~ symbol represents any type of bond regardless of the stereochemistry; and the respective enantiomers, other stereochemical isomers, hydrates, solvates, tautomers and pharmaceutically acceptable salts of said compounds.

In another aspect of the present invention methods of using the compounds having the general structure shown in Formula (XIX) below:

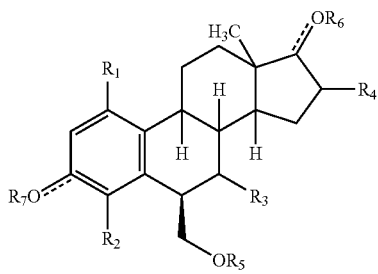

wherein: $R_1$, $R_2$, $R_3$, $R_4$, $R_5$, $R_6$, $R_7$ are as described above, and the ---- symbol represents either a single or a double bond with the proviso that when the ---- symbol is a double bond and forms a keto group at position 3 or 17, then no $R_7$ or $R_6$ is respectively present.

In at least another aspect of the present invention, effective doses of compounds having Formulas (I)-(II) are administered to the patients in need of such therapy:

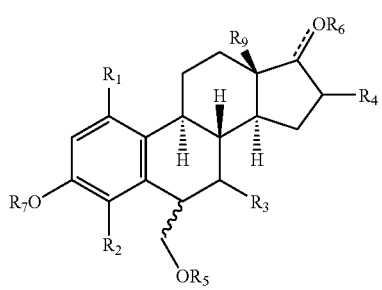

Formula (I)

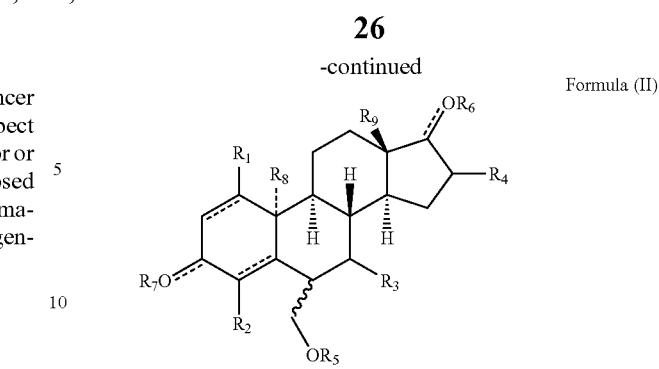

Formula (II)

wherein $R_1$, $R_2$, $R_3$, $R_4$, $R_5$, $R_6$, $R_7$, $R_8$ and $R_9$ are as described above; and the ---- symbol represents either a single or a double bond and when the ---- symbol is a double bond and forms a keto group at position 3 or 17, then no $R_7$ or $R_6$ is present, respectively; the symbol --- represent the presence or absence of a bond at position 10; and the ~~~ symbol represents any type of bond regardless of the stereochemistry.

These methods may be used to treat any tumor which may be either directly or indirectly effected by hormonal and/or estrogen-related activity, including but not in any way limited to solid tumors associated with breast, pancreatic, lung, colon, prostate, ovarian cancers, as well as brain, liver, spleen, kidney, lymph node, small intestine, blood cells, bone, stomach, endometrium, testicular, ovary, central nervous system, skin, head and neck, esophagus, or bone marrow cancer; as well as hematological cancers, such as leukemia, acute promyelocytic leukemia, lymphoma, multiple myeloma, myelodysplasia, myeloproliferative disease, or refractory anemia.

Among other things, the inventor of the present invention offer a new mode of action for treating estrogen dependent or independent tumors. Traditional approach employed drugs once bound to the ERs modified the ERs configuration to the extent that in effect rendered them destroyed. Accordingly, destruction of such bound ERs would cease transmission of all external and internal signals essential for vitality of the cells; creating a stop in cellular growth.

It is believed that the presently disclosed compounds are able to bind to number of receptors including the estrogen, testosterone and androgen receptors. The inventor has unexpectedly observed that upon binding, the compounds of the present invention are able to modulate the cellular first or second messenger signaling pathways and further potentiate their clinical effects through gene dependent or gene independent mechanisms, e.g. gene dependent estrogen activity has been well described in the art and those of ordinary skill in the art are able to ascertain the pathways involved inactivation of a estrogen dependent gene.

However, in the present invention, the inventor has unexpectedly found that the compounds of the claimed invention are able to modulate cellular activity at a level independent of the traditional gene regulated mechanisms. In this aspect of the invention, the compounds of the instant invention are capable of binding directly to multiple steroid receptors at the plasma membrane and trigger internal cell mediated stress mechanisms involving the unfolded protein response ("UPR") at the endoplasmic reticulum. The UPR stress response subsequently lead to growth inhibition, and cell death through modulation of stress response genes such as CHOP also known as GADD153, TRIB3, etc.

In addition, administration of the compounds of the present invention for treatment of various cancer states may comprise administration of a compound of Formula (I) in combination with other adjunct cancer therapies, such as chemotherapy, radiotherapy, gene therapy, hormone therapy and other cancer therapies known in the art. Combinations of the presently disclosed compounds with other anti-cancer or chemotherapeutic agents are within the scope of the invention. Examples of such agents can be found in *Cancer Principles and Practice of Oncology* by V. T. Devita and S. Hellman (editors), 6th edition (Feb. 15, 2001), Lippincott Williams & Wilkins Publishers. A physician, veterinarian or clinician of ordinary skill in the art would be able to discern which combinations of agents would be useful based on the particular characteristics of the drugs and the cancer involved. Such anti-cancer agents include the following: estrogen receptor modulators, androgen receptor modulators, retinoid receptor modulators, cytotoxic agents, anti-proliferative agents, prenyl-protein transferase inhibitors, HMG-CoA reductase inhibitors, EHV protease inhibitors, reverse transcriptase inhibitors, aromatase inhibitors, and angiogenesis inhibitors.

Exemplified Compounds

In at least one aspect of the invention, inventors illustrate the compounds of the present invention in table I below:

TABLE I

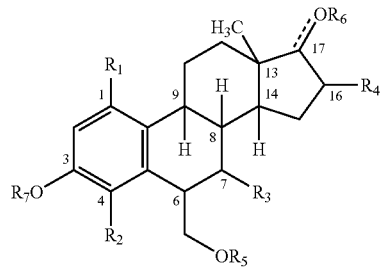

$R_1, R_2, R_3, R_4$: independently H, $C_1$-$C_6$ alkyl, substituted alkyl, or halogen
$R_5, R_7$: H, $C_1$-$C_6$ alkyl, substituted alkyl, sulfate, or glucuronide
$R_6$: H, $C_1$-$C_6$ alkyl, or substituted alkyl, sulfate, or glucuronide, when ----- is a single bond; not present, when ----- is a double bond

| Entry | Substituents | | | Spatial Configuration | | | | | |
|---|---|---|---|---|---|---|---|---|---|
| | $R_5$ | $R_6$ | $R_7$ | C-6 | C-8 | C-9 | C-13 | C-14 | C-17 |
| 1 | H | H | H | S | S | S | S | S | S |
| 2 | H | H | H | S | R | R | R | R | R |
| 3 | H | H | H | S | S | S | S | S | R |
| 4 | H | H | H | S | R | R | R | R | S |
| 5 | H | — | H | S | S | S | S | S | C=O |
| 6 | H | — | H | S | R | R | R | R | C=O |
| 7 | H | H | H | R | R | R | R | R | R |
| 8 | H | H | H | R | S | S | S | S | S |
| 9 | H | H | H | R | S | S | S | S | R |
| 10 | H | H | H | R | R | R | R | R | S |
| 11 | H | — | H | R | S | S | S | S | C=O |
| 12 | H | — | H | R | R | R | R | R | C=O |
| 13 | Me | H | H | S | S | S | S | S | S |
| 14 | Me | H | H | S | R | R | R | R | R |
| 15* | Me | H | H | S | S | S | S | S | R |
| 16 | Me | H | H | S | R | R | R | R | S |
| 17 | Me | — | H | S | S | S | S | S | C=O |
| 18 | Me | — | H | S | R | R | R | R | C=O |
| 19 | Me | H | H | R | R | R | R | R | R |
| 20** | Me | H | H | R | S | S | S | S | S |
| 21 | Me | H | H | R | S | S | S | S | R |
| 22 | Me | H | H | R | R | R | R | R | S |
| 23 | Me | — | H | R | S | S | S | S | C=O |
| 24 | Me | — | H | R | R | R | R | R | C=O |
| 25 | H | H | $SO_3H$ | S | S | S | S | S | S |
| 26 | H | H | $SO_3H$ | S | R | R | R | R | R |
| 27 | H | H | $SO_3H$ | S | S | S | S | S | R |
| 28 | H | H | $SO_3H$ | S | R | R | R | R | S |
| 29 | H | — | $SO_3H$ | S | S | S | S | S | C=O |
| 30 | H | — | $SO_3H$ | S | R | R | R | R | C=O |
| 31 | H | H | $SO_3H$ | R | R | R | R | R | R |

TABLE I-continued

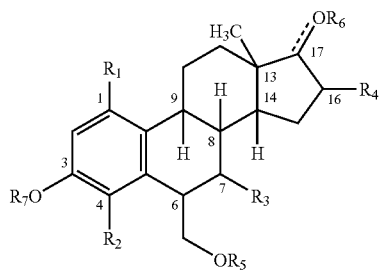

$R_1, R_2, R_3, R_4$: independently H, $C_1$-$C_6$ alkyl, substituted alkyl, or halogen
$R_5, R_7$: H, $C_1$-$C_6$ alkyl, substituted alkyl, sulfate, or glucuronide
$R_6$: H, $C_1$-$C_6$ alkyl, or substituted alkyl, sulfate, or glucuronide, when ----- is a single bond; not present, when ----- is a double bond

| Entry | Substituents | | | Spatial Configuration | | | | | |
|---|---|---|---|---|---|---|---|---|---|
| | $R_5$ | $R_6$ | $R_7$ | C-6 | C-8 | C-9 | C-13 | C-14 | C-17 |
| 32 | H | H | $SO_3H$ | R | S | S | S | S | S |
| 33 | H | H | $SO_3H$ | R | S | S | S | S | R |
| 34 | H | H | $SO_3H$ | R | R | R | R | R | S |
| 35 | H | — | $SO_3H$ | R | S | S | S | S | C=O |
| 36 | H | — | $SO_3H$ | R | R | R | R | R | C=O |
| 37 | Me | H | $SO_3H$ | S | S | S | S | S | S |
| 38 | Me | H | $SO_3H$ | S | R | R | R | R | R |
| 39 | Me | H | $SO_3H$ | S | S | S | S | S | R |
| 40 | Me | H | $SO_3H$ | S | R | R | R | R | S |
| 41 | Me | — | $SO_3H$ | S | S | S | S | S | C=O |
| 42 | Me | — | $SO_3H$ | S | R | R | R | R | C=O |
| 43 | Me | H | $SO_3H$ | R | R | R | R | R | R |
| 44 | Me | H | $SO_3H$ | R | S | S | S | S | S |
| 45 | Me | H | $SO_3H$ | R | S | S | S | S | R |
| 46 | Me | H | $SO_3H$ | R | R | R | R | R | S |
| 47 | Me | — | $SO_3H$ | R | S | S | S | S | C=O |
| 48 | Me | — | $SO_3H$ | R | R | R | R | R | C=O |
| 49 | H | H | glucuronide | S | S | S | S | S | S |
| 50 | H | H | glucuronide | S | R | R | R | R | R |
| 51 | H | H | glucuronide | S | S | S | S | S | R |
| 52 | H | H | glucuronide | S | R | R | R | R | S |
| 53 | H | — | glucuronide | S | S | S | S | S | C=O |
| 54 | H | — | glucuronide | S | R | R | R | R | C=O |
| 55 | H | H | glucuronide | R | R | R | R | R | R |
| 56 | H | H | glucuronide | R | S | S | S | S | S |
| 57 | H | H | glucuronide | R | S | S | S | S | R |
| 58 | H | H | glucuronide | R | R | R | R | R | S |
| 59 | H | — | glucuronide | R | S | S | S | S | C=O |
| 60 | H | — | glucuronide | R | R | R | R | R | C=O |
| 61 | Me | H | glucuronide | S | S | S | S | S | S |
| 62 | Me | H | glucuronide | S | R | R | R | R | R |
| 63 | Me | H | glucuronide | S | S | S | S | S | R |
| 64 | Me | H | glucuronide | S | R | R | R | R | S |
| 65 | Me | — | glucuronide | S | S | S | S | S | C=O |
| 66 | Me | — | glucuronide | S | R | R | R | R | C=O |
| 67 | Me | H | glucuronide | R | R | R | R | R | R |
| 68 | Me | H | glucuronide | R | S | S | S | S | S |
| 69 | Me | H | glucuronide | R | S | S | S | S | R |
| 70 | Me | H | glucuronide | R | R | R | R | R | S |
| 71 | Me | — | glucuronide | R | S | S | S | S | C=O |
| 72 | Me | — | glucuronide | R | R | R | R | R | C=O |

*NDC-1033;
**NDC-1022

The preferred compounds in Table I include compounds 15 and 20. At least one aspect of the instant invention is directed to these preferred compound, their method of use and making.

In at least another aspect of the invention, inventors illustrate the compounds of the present invention in table II below:

TABLE II

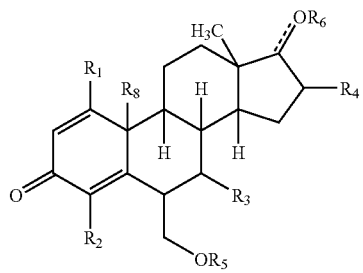

R$_1$, R$_2$, R$_3$, R$_4$: independently H, C$_1$-C$_6$ alkyl, substituted alkyl, or halogen
R$_5$: H, C$_1$-C$_6$ alkyl, substituted alkyl, sulfate, or glucuronide
R$_6$: H, C$_1$-C$_6$ alkyl, or substituted alkyl, sulfate, or glucuronide,
R$_8$: H, C$_1$-C$_6$ alkyl, or substituted alkyl,
when ----- is a single bond; not present, when ----- is a double bond

| Entry | Substituent R$_5$ | R$_6$ | C-6 | C-8 | C-9 | C-10 | C-13 | C-14 | C-17 |
|---|---|---|---|---|---|---|---|---|---|
| 73 | H | H | S | S | S | R | S | S | S |
| 74 | H | H | S | R | R | R | R | R | R |
| 75 | H | H | S | S | S | R | S | S | R |
| 76 | H | H | S | R | R | R | R | R | S |
| 77 | H | — | S | S | S | R | S | S | C=O |
| 78 | H | — | S | R | R | R | R | R | C=O |
| 79 | H | H | R | S | S | R | S | S | R |
| 80 | H | H | R | S | S | R | S | S | S |
| 81 | H | H | R | S | S | R | S | S | R |
| 82 | H | H | R | R | R | R | R | R | S |
| 83 | H | — | R | S | S | R | S | S | C=O |
| 84 | H | — | R | R | R | R | R | R | C=O |
| 85 | Me | H | S | S | S | R | S | S | S |
| 86 | Me | H | S | R | R | R | R | R | R |
| 87 | Me | H | S | S | S | R | S | S | R |
| 88 | Me | H | S | R | R | R | R | R | S |
| 89* | Me | — | S | S | S | R | S | S | C=O |
| 90** | Me | — | R | R | R | R | R | S | C=O |
| 91 | Me | H | R | R | R | R | R | R | R |
| 92 | Me | H | S | S | S | S | S | S | S |
| 93 | Me | H | S | R | R | R | R | R | R |
| 94 | Me | H | S | S | S | S | S | S | R |
| 95 | Me | H | S | R | R | R | R | R | S |
| 96 | Me | — | R | R | S | — | R | S | C=O |
| 97 | Me | — | S | R | R | R | R | R | C=O |
| 98*** | Me | H | S | R | R | S | R | S | R |
| 99 | Me | H | R | S | S | S | S | S | S |
| 100 | Me | H | R | S | S | S | S | S | R |
| 101 | Me | H | R | R | R | S | R | R | S |
| 102 | Me | — | R | R | S | R | S | S | C=O |
| 103 | Me | — | R | R | R | R | R | R | C=O |
| 104 | H | H | S | S | S | R | S | S | S |
| 105 | H | H | S | R | R | R | R | R | R |
| 106 | H | H | S | S | S | R | S | S | R |
| 107 | H | H | S | R | R | R | R | R | S |
| 108 | H | — | S | S | S | R | S | S | C=O |
| 109 | H | — | S | R | R | R | R | R | C=O |
| 110 | H | H | R | R | R | R | R | R | R |
| 111 | H | H | R | S | S | R | S | S | S |
| 112 | H | H | R | S | S | R | S | S | R |
| 113 | H | H | R | R | R | R | R | R | S |
| 114 | H | — | R | S | S | R | S | S | C=O |
| 115 | H | — | R | R | R | R | R | R | C=O |
| 116 | Me | H | S | S | S | R | S | S | S |
| 117 | Me | H | S | R | R | R | R | R | R |
| 118 | Me | H | S | S | S | R | S | S | R |
| 119 | Me | H | S | R | R | R | R | S | S |
| 120 | Me | — | S | S | S | S | S | S | C=O |
| 121 | Me | — | S | R | R | R | R | R | C=O |
| 122 | Me | H | R | R | R | R | R | R | R |
| 123 | Me | H | R | S | S | R | S | S | S |
| 124 | Me | H | R | S | S | S | S | S | R |
| 125 | Me | H | R | R | R | S | R | R | S |

TABLE II-continued

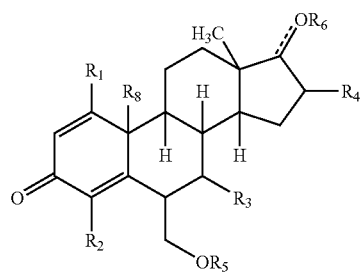

R$_1$, R$_2$, R$_3$, R$_4$: independently H, C$_1$-C$_6$ alkyl, substituted alkyl, or halogen
R$_5$: H, C$_1$-C$_6$ alkyl, substituted alkyl, sulfate, or glucuronide
R$_6$: H, C$_1$-C$_6$ alkyl, or substituted alkyl, sulfate, or glucuronide,
R$_8$: H, C$_1$-C$_6$ alkyl, or substituted alkyl,
when ----- is a single bond; not present, when ----- is a double bond

| Entry | Substituent R$_5$ | R$_6$ | C-6 | C-8 | C-9 | C-10 | C-13 | C-14 | C-17 |
|---|---|---|---|---|---|---|---|---|---|
| 126 | Me | — | R | S | S | R | S | S | C=O |
| 127 | Me | — | R | R | R | R | R | R | C=O |
| 128**** | Me | H | R | R | S | R | R | S | R |

*NDC-1077, when R$_8$ is a methyl;
**NDC-1011, when R$_8$ is a methyl;
***NDC-1110, when R$_8$ is a methyl;
****NDC-1044, when R$_8$ is a methyl.

The preferred compounds in Table II include compounds 89, 90, 98, and 128. At least one aspect of the instant invention is directed to these preferred compound, their method of use and making.

One specific non-limiting example for treatment of an identified cancer state as described herein includes use a compound of Formula (I), which has the Formula (IX) below:

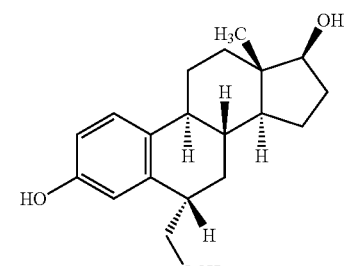

(IX) A - NDC-1033

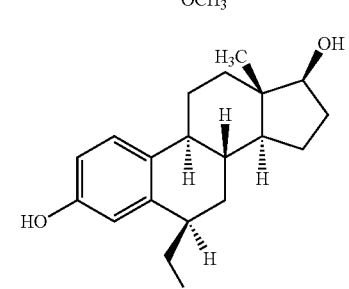

(IX) B - NDC-1022

Another specific non-limiting example for treatment of an identified cancer state as described herein includes use a compound of Formula (I), which has the Formula (X), below:

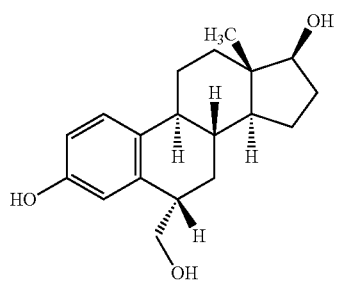

(X) A - NDC-1066

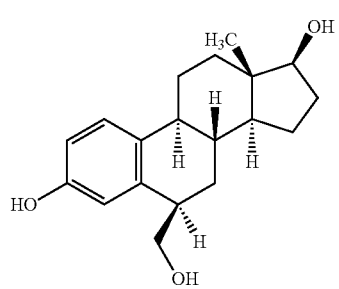

(X) B - NDC-1055

In at least another aspect of the invention, inventors illustrate the compounds of the present invention in table II below:

TABLE III

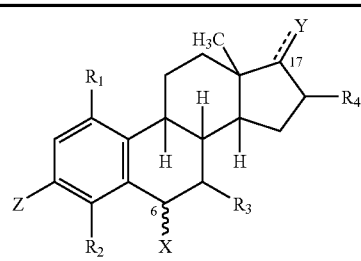

$R_1, R_2, R_3, R_4$: independently H, $C_1$-$C_6$ alkyl, substituted alkyl, or halogen and ----- is a single or double bond; not present.

| Entry | X | Z | Y | C-6 | C-17 |
|---|---|---|---|---|---|
| 129 | CH₂OH | OH | OH | S | S |
| 130 | CH₂OH | OH | OH | S | R |
| 131 | CH₂OH | OH | OH | R | R |
| 132 | CH₂OH | OH | OH | R | S |
| 133 | CH₂ONH₂ | OH | OH | S | S |
| 134 | CH₂ONH₂ | OH | OH | S | R |
| 135 | CH₂ONH₂ | OH | OH | R | R |
| 136 | CH₂ONH₂ | OH | OH | R | S |
| 137 | CH₂ONHMe | OH | OH | S | S |
| 138 | CH₂ONHMe | OH | OH | S | R |
| 139 | CH₂ONHMe | OH | OH | R | R |
| 140 | CH₂ONHMe | OH | OH | R | S |
| 141 | CH₂ONMe₂ | OH | OH | S | S |
| 142 | CH₂ONMe₂ | OH | OH | S | R |
| 143 | CH₂ONMe₂ | OH | OH | R | R |
| 144 | CH₂ONMe₂ | OH | OH | R | S |
| 145 | CH₂ONHAc | OH | OH | S | S |
| 146 | CH₂ONHAc | OH | OH | S | R |
| 147 | CH₂ONHAc | OH | OH | R | R |
| 148 | CH₂ONHAc | OH | OH | R | S |
| 149 | CH₂NH₂ | OH | OH | S | S |
| 150 | CH₂NH₂ | OH | OH | S | R |
| 151 | CH₂NH₂ | OH | OH | R | R |
| 152 | CH₂NH₂ | OH | OH | R | S |
| 153 | CH₂NHMe | OH | OH | S | S |
| 154 | CH₂NHMe | OH | OH | S | R |
| 155 | CH₂NHMe | OH | OH | R | R |
| 156 | CH₂NHMe | OH | OH | R | S |

TABLE III-continued

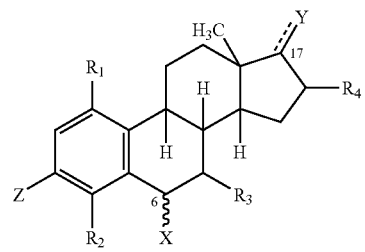

$R_1, R_2, R_3, R_4$: independently H, $C_1$-$C_6$ alkyl, substituted alkyl, or halogen and ----- is a single or double bond; not present.

| Entry | X | Z | Y | C-6 | C-17 |
|---|---|---|---|---|---|
| 157 | CH₂NMe₂ | OH | OH | S | S |
| 158 | CH₂NMe₂ | OH | OH | S | R |
| 159 | CH₂NMe₂ | OH | OH | R | R |
| 160 | CH₂NMe₂ | OH | OH | R | S |
| 161 | CH₂NHAc | OH | OH | S | S |
| 162 | CH₂NHAc | OH | OH | S | R |
| 163 | CH₂NHAc | OH | OH | R | R |
| 164 | CH₂NHAc | OH | OH | R | S |
| 165 | CH₂NHOH | OH | OH | S | S |
| 166 | CH₂NHOH | OH | OH | S | R |
| 167 | CH₂NHOH | OH | OH | R | R |
| 168 | CH₂NHOH | OH | OH | R | S |
| 169 | CH₂NHOMe | OH | OH | S | S |
| 170 | CH₂NHOMe | OH | OH | S | R |
| 171 | CH₂NHOMe | OH | OH | R | R |
| 172 | CH₂NHOMe | OH | OH | R | S |
| 173 | CH₂NHNH₂ | OH | OH | S | S |
| 174 | CH₂NHNH₂ | OH | OH | S | R |
| 175 | CH₂NHNH₂ | OH | OH | R | R |
| 176 | CH₂NHNH₂ | OH | OH | R | S |
| 177 | CH₂NHNHMe | OH | OH | S | S |
| 178 | CH₂NHNHMe | OH | OH | S | R |
| 179 | CH₂NHNHMe | OH | OH | R | R |
| 180 | CH₂NHNHMe | OH | OH | R | S |
| 181 | CH₂NHNMe₂ | OH | OH | S | S |
| 182 | CH₂NHNMe₂ | OH | OH | S | R |
| 183 | CH₂NHNMe₂ | OH | OH | R | R |
| 184 | CH₂NHNMe₂ | OH | OH | R | S |
| 185 | CH₂NHNHAc | OH | OH | S | S |
| 186 | CH₂NHNHAc | OH | OH | S | R |
| 187 | CH₂NHNHAc | OH | OH | R | R |
| 188 | CH₂NHNHAc | OH | OH | R | S |
| 189 | CH₂N(Me)NH₂ | OH | OH | S | S |
| 190 | CH₂N(Me)NH₂ | OH | OH | S | R |
| 191 | CH₂N(Me)NH₂ | OH | OH | R | R |
| 192 | CH₂N(Me)NH₂ | OH | OH | R | S |
| 193 | CH₂N(Me)NHMe | OH | OH | S | S |
| 194 | CH₂N(Me)NHMe | OH | OH | S | R |
| 195 | CH₂N(Me)NHMe | OH | OH | R | R |
| 196 | CH₂N(Me)NHMe | OH | OH | R | S |
| 197 | CH₂N(Me)NHAc | OH | OH | S | S |
| 198 | CH₂N(Me)NHAc | OH | OH | S | R |
| 199 | CH₂N(Me)NHAc | OH | OH | R | R |
| 200 | CH₂N(Me)NHAc | OH | OH | R | S |
| 201 | OCH₂NH₂ | OH | OH | S | S |
| 202 | OCH₂NH₂ | OH | OH | S | R |
| 203 | OCH₂NH₂ | OH | OH | R | R |
| 204 | OCH₂NH₂ | OH | OH | R | S |
| 205 | OCH₂NHMe | OH | OH | S | S |
| 206 | OCH₂NHMe | OH | OH | S | R |
| 207 | OCH₂NHMe | OH | OH | R | R |
| 208 | OCH₂NHMe | OH | OH | R | S |
| 209 | OCH₂NHAc | OH | OH | S | S |
| 210 | OCH₂NHAc | OH | OH | S | R |
| 211 | OCH₂NHAc | OH | OH | R | R |
| 212 | OCH₂NHAc | OH | OH | R | S |
| 213 | NHCH₂OH | OH | OH | S | S |
| 214 | NHCH₂OH | OH | OH | S | R |
| 215 | NHCH₂OH | OH | OH | R | R |
| 216 | NHCH₂OH | OH | OH | R | S |
| 217 | NHCH₂OMe | OH | OH | S | S |
| 218 | NHCH₂OMe | OH | OH | S | R |

TABLE III-continued

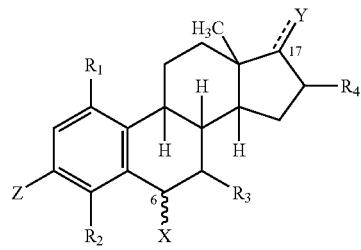

$R_1$, $R_2$, $R_3$, $R_4$: independently H, $C_1$-$C_6$ alkyl, substituted alkyl, or halogen and ----- is a single or double bond; not present.

| Entry | X | Z | Y | C-6 | C-17 |
|---|---|---|---|---|---|
| 219 | NHCH$_2$OMe | OH | OH | R | R |
| 220 | NHCH$_2$OMe | OH | OH | R | S |
| 221 | NHCH$_2$OAc | OH | OH | S | S |
| 222 | NHCH$_2$OAc | OH | OH | S | R |
| 223 | NHCH$_2$OAc | OH | OH | R | R |
| 224 | NHCH$_2$OAc | OH | OH | R | S |
| 225 | NHCH$_2$NH$_2$ | OH | OH | S | S |
| 226 | NHCH$_2$NH$_2$ | OH | OH | S | R |
| 227 | NHCH$_2$NH$_2$ | OH | OH | R | R |
| 228 | NHCH$_2$NH$_2$ | OH | OH | R | S |
| 229 | NHCH$_2$NHMe | OH | OH | S | S |
| 230 | NHCH$_2$NHMe | OH | OH | S | R |
| 231 | NHCH$_2$NHMe | OH | OH | R | R |
| 232 | NHCH$_2$NHMe | OH | OH | R | S |
| 233 | NHCH$_2$NMe$_2$ | OH | OH | S | S |
| 234 | NHCH$_2$NMe$_2$ | OH | OH | S | R |
| 235 | NHCH$_2$NMe$_2$ | OH | OH | R | R |
| 236 | NHCH$_2$NMe$_2$ | OH | OH | R | S |
| 237 | NHCH$_2$NHAc | OH | OH | S | S |
| 238 | NHCH$_2$NHAc | OH | OH | S | R |
| 239 | NHCH$_2$NHAc | OH | OH | R | R |
| 240 | NHCH$_2$NHAc | OH | OH | R | S |
| 241 | N(Me)CH$_2$OH | OH | OH | S | S |
| 242 | N(Me)CH$_2$OH | OH | OH | S | R |
| 243 | N(Me)CH$_2$OH | OH | OH | R | R |
| 244 | N(Me)CH$_2$OH | OH | OH | R | S |
| 245 | N(Me)CH$_2$OMe | OH | OH | S | S |
| 246 | N(Me)CH$_2$OMe | OH | OH | S | R |
| 247 | N(Me)CH$_2$OMe | OH | OH | R | R |
| 248 | N(Me)CH$_2$OMe | OH | OH | R | S |
| 249 | N(Me)CH$_2$OAc | OH | OH | S | S |
| 250 | N(Me)CH$_2$OAc | OH | OH | S | R |
| 251 | N(Me)CH$_2$OAc | OH | OH | R | R |
| 252 | N(Me)CH$_2$OAc | OH | OH | R | S |
| 253 | N(Me)CH$_2$NH$_2$ | OH | OH | S | S |
| 254 | N(Me)CH$_2$NH$_2$ | OH | OH | S | R |
| 255 | N(Me)CH$_2$NH$_2$ | OH | OH | R | R |
| 256 | N(Me)CH$_2$NH$_2$ | OH | OH | R | S |
| 257 | N(Me)CH$_2$NHMe | OH | OH | S | S |
| 258 | N(Me)CH$_2$NHMe | OH | OH | S | R |
| 259 | N(Me)CH$_2$NHMe | OH | OH | R | R |
| 260 | N(Me)CH$_2$NHMe | OH | OH | R | S |
| 261 | N(Me)CH$_2$NMe$_2$ | OH | OH | S | S |
| 262 | N(Me)CH$_2$NMe$_2$ | OH | OH | S | R |
| 263 | N(Me)CH$_2$NMe$_2$ | OH | OH | R | R |
| 264 | N(Me)CH$_2$NMe$_2$ | OH | OH | R | S |
| 265 | N(Me)CH$_2$NHAc | OH | OH | S | S |
| 266 | N(Me)CH$_2$NHAc | OH | OH | S | R |
| 267 | N(Me)CH$_2$NHAc | OH | OH | R | R |
| 268 | N(Me)CH$_2$NHAc | OH | OH | R | S |

The above active compounds may also be used as part of an in vitro assay, for example, in order to determine whether a candidate host is likely to benefit from treatment with the compound in question. Any active compound of the present invention may also be used as a standard, for example, in an assay, in order to identify other active compounds, other anti-proliferative agents, other anti-inflammatory agents, etc.

At least in one aspect of the instant invention, the candidate compounds were evaluated for their estrogen receptor antagonistic activity. The evaluation as to whether a compound is an estrogen receptor antagonist may be carried out by various methodologies known in the art. In the instant application, such capacity was determined by conducting the Luciferase binding assay according to the screening methods described herein.

In a more preferred embodiment of this aspect of the invention, the estrogen receptor binding capacity were assessed by transiently transfecting CV-1 cells with expression constructs for either ER($\alpha$) or ER ($\beta$) plus an ERE-tk-luciferase reporter construct. The cells were then divided into controls and candidate groups wherein the controls received no treatment, or were treated with estradiol alone (1 nM) and the candidate groups received estradiol plus an Endece compound at varying concentrations. After 16-24 hours the cells were harvested and assayed for luciferase activity using a commercially available assay kit.

In yet another aspect of the instant invention, the $IC_{50}$ or the half maximal inhibitory concentration of the candidate compounds were determined to assess drug potency and potential dosing regimens for in vivo use. One of ordinary skill in the art is readily able to ascertain such information using commonly known methodologies. As it has been well described in the art, $IC_{50}$ represents and measures how much of a particular substance/molecule is needed to inhibit some biological process by 50%. In the instant case, the $IC_{50}$ of the candidate compounds were determined as the concentration that led to a response of 50% compared to the vehicle control cells.

As noted herein, the salts of the compounds of this invention refer to non-toxic "pharmaceutically acceptable salts." Other salts may, however, be useful in the preparation of the compounds according to the invention or of their pharmaceutically acceptable salts. When the compounds of the present invention contain a basic group, salts encompassed within the term "pharmaceutically acceptable salts" refer to non-toxic salts which are generally prepared by reacting the free base with a suitable organic or inorganic acid. Representative salts include any such salt known in the art. Where compounds of the present invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts.

To treat a mammalian subject, such as a human patient, an effective amount of one or more compounds of the present invention, or a pharmaceutically-acceptable salt thereof, is administered to the mammalian subject so as to promote exposure to or contact of cancer cells or the targeted tumor growth. Effective dosage forms, modes of administration and dosage amounts may be determined empirically, and making such determinations is within the skill of the art. It is understood by the physician, veterinarian or clinician of ordinary skill in the art that the dosage amount will vary with the activity of the particular compound employed, course and/or progression of the disease state, the route of administration, the rate of excretion of the compound, renal and hepatic function of the patient, the duration of the treatment, the identity of any other drugs being administered to the subject, age, size and like factors well known in the medical arts. As discussed herein, the compounds of the present invention can be administered in such oral dosage forms as tablets, capsules (each of which includes sustained release or timed release formulations), pills, powders, micronized compositions, granules, elixirs, tinctures, suspensions, syrups and emulsions. Likewise, they may also be administered in intravenous (bolus or infusion), intraperitoneal, topical (e.g., ocular eyedrop), subcutaneous, intramuscular or transdermal (e.g., patch) form, all using forms well known to those of ordinary skill in the pharmaceutical arts. Again, the ordinarily skilled physician, veterinarian or clinician can readily determine and prescribe the effective amount of the drug required to prevent, counter or arrest the progress of the condition.

Oral dosages of the present invention, when used for the indicated effects, will range between about 0.01 mg per kg of body weight per day (mg/kg/day) to about 100 mg/kg/day, preferably 0.01 to 10 mg/kg/day, and most preferably 0.1 to 5.0 mg/kg/day. For oral administration, the compositions are preferably provided in the form of tablets containing 0.01, 0.05, 0.1, 0.5, 1.0, 2.5, 5.0, 10.0, 15.0, 25.0, 50.0, 100 and 500 milligrams of the active ingredient for the symptomatic adjustment of the dosage to the patient to be treated. A medicament typically contains from about 0.01 mg to about 500 mg of the active ingredient, preferably, from about 1 mg to about 100 mg of active ingredient. Intravenously, the most preferred doses will range from about 0.1 to about 10 mg/kg/minute during a constant rate infusion. Compounds of the present invention may be administered in a single daily dose, or the total daily dosage may be administered in divided doses of two, three or four times daily.

As noted herein, the compounds of the present invention can be used in combination with other anti-cancer agents or other agents which will enhance the treatment regime for the mammalian subject. The individual components of such combinations can be administered separately at different times during the course of therapy or concurrently in divided or single combination forms to patients or regions of such patients in need of such therapy. The instant invention is therefore to be understood as embracing all such regimes of simultaneous or alternating treatment and the term "administering" is to be interpreted accordingly. It will be understood that the scope of combinations of the compounds of this invention with other agents useful to treat the targeted cancer condition includes in principle any combination with any pharmaceutical composition useful for treating disorders related to estrogen functioning.

It may be convenient or desirable to prepare, purify, and/or handle the active compound in the form of a prodrug. The term "prodrug" as used herein, pertains to a compound which, when metabolized, yields the desired active compound or in itself is the active compound. This includes for example adding a phosphoric acid ester moiety in suitable positions such as positions 3, 6, 10 or 17. Typically, the prodrug is inactive, or less active than the active compound, but may provide advantageous handling, administration, or metabolic properties. For example, some prodrugs are ethers of the active compound; during metabolism the ether group is cleaved to yield the active drug. Also, some prodrugs are activated enzymatically to yield the active compound, or a compound which, upon further chemical reaction, yields the active compound. Thus, in the methods of treatment of the present invention disclosed herein, the term "administering" shall encompass the treatment of the various conditions described with the compound specifically disclosed or with a compound which may not be specifically disclosed, but which converts to the specified compound in vivo after administration to the patient. Metabolites of these compounds include active species produced upon introduction of compounds of this invention into the mammalian subject.

Compounds of the present invention may be prodrugs for potent anti-proliferative agents. Compounds which exhibit low or moderate intrinsic activity may act as prodrugs, and be metabolically activated (e.g., in vivo) to generate more potent compounds. This is especially useful in cancer therapy where metabolic activation can be achieved by an enzyme that is expressed in tumors. Prodrugs, acting as a substrate, may be metabolized by CYP19, 17β-HSD, HS-demethylase or another steroidal linked enzyme to generate a potent anti-cancer agent. The (R) or (S)-6-methyloxoalkyl derivatives of exemestane suggest that it may be active against numerous forms of cancer beyond breast cancer. Activity in inhibiting tumor cell growth in cells lines derived from breast, lung, colon, prostate, endometrial and ovarian cancers was observed for the NDC-1011 enantiomer. For example, in vitro studies of tumor cell growth is the highest in cell lines that are CYP19 positive (MDA-MB-213 and SK-OV-3) and is reduced in those cell lines that are CYP19 negative (MCF-7 and NIH:OVCAR-3) indicates that NDC-1011 may act as a pro-drug. See Formula (XI) and (XII) below for the structure of NDC-1077 and NDC-1011.

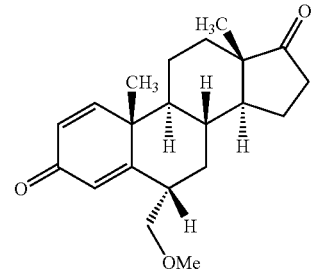

(XI) NDC-1077

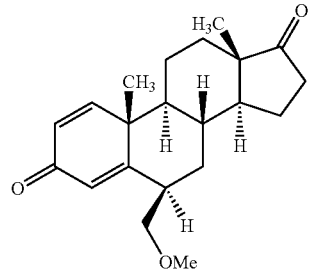

(XII) NDC-1011

While not bound by any theory, for example, if NDC-1011 is a pro-drug, then any number of the body's normal steroidogenic enzymes should be active towards the NDC-1011 compound thereby converting NDC-1011 into the active metabolite(s). This aspect of the invention can apply in the same manner to both the S and the R diastereomers.

The prodrug compounds of the instant invention act in a manner analogous to that observed for endogenous androstenedione, NDC-1011 is converted to an aromatic ring by hydroxylation at the C-3 carbon of NDC-1011 via CYP19 to give rise to the metabolite NDC-1099. see FIG. 1 in the Estradiol biosynthetic pathway wherein Androstendione is converted to the Estrone via CYP19. NDC-1099 could undergo further hydroxylation at the C-17 carbon via the reversible action of 17β-hydroxysteroid dehydrogenase (17β-HSD) resulting in the diol compound NDC-1022.

As with Estradiol, the diol compound NDC-1022 has an aromatic ring, but differs from estradiol with respect to the methyloxyalkyl substituent at the C-6 carbon. The metabolism of NDC-1011 into the diol compound NDC-1022 could occur in any order as shown in FIG. 2. For example, NDC-1044 formed by 17β-HSD is converted to the NDC-1022 diol by CYP19 aromatization activity.

Without being bound to any theories, it has been reported that Estradiol binds to the receptor ligand pocket of estrogen receptors (both ERα and ERβ), via the C17-OH (via His 524);

and the C3-OH (via Arg 394 and Glu 353). As with Estradiol, binding of NDC-1022 diol in the same ligand pocket of ERα and ERβ via similar amino acid bindings may occur. Additionally, the presence of the methyloxyalkyl substituent at the C-6 carbon of compound NDC-1022 may alter the conformation of the normal ligand-bound receptor resulting in modified activity accounting for the observed anti-tumor activity.

In addition, demethylase enzyme activity directed at the C-6 methyl group of NDC-1011 (or one of the metabolites of NDC-1011), may indicate the formation of triol metabolite NDC-1055. With alcohol groups at the C-3, C-6 and C-17 carbons, such an NDC-1055 triol metabolite may bind to a broad spectrum of steroid receptors in a range of tissues involving various combinations of the C-3, C-6 and C-17 alcohols. One example of such metabolites includes the compound of Formula (VII)B as shown below:

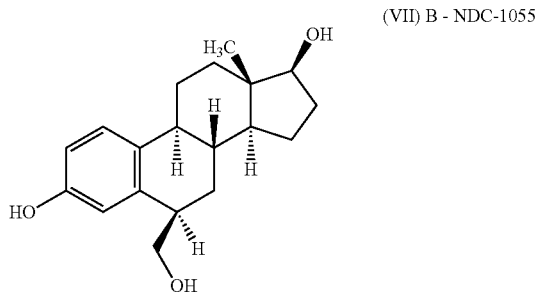

(VII) B - NDC-1055

Compositions

As used herein, the term "composition" is intended to encompass a product comprising the specified ingredients in the specified amounts, as well as any product which results, directly or indirectly, from combination of the specified ingredients in the specified amounts.

Pharmaceutical formulations of the present invention include those suitable for oral, nasal, topical (including buccal and sublingual), rectal, vaginal and/or parenteral administration. Regardless of the route of administration selected, the active ingredient(s) are formulated into pharmaceutically-acceptable dosage forms by conventional methods known to those of skill in the art.

The amount of the active ingredient(s) which will be combined with a carrier material to produce a single dosage form will vary depending upon the host being treated, the particular mode of administration and all of the other factors described above. The amount of the active ingredient(s) which will be combined with a carrier material to produce a single dosage form will generally be that amount of the active ingredient(s) which is the lowest dose effective to produce a therapeutic effect.

Methods of preparing pharmaceutical formulations or compositions include the step of bringing the active ingredient(s) into association with the carrier and, optionally, one or more accessory ingredients. In general, the formulations are prepared by uniformly and intimately bringing the active ingredient(s) into association with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or nonaqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of the active ingredient(s). The active ingredient(s) may also be administered as a bolus, electuary or paste.

In solid dosage forms of the invention for oral administration (capsules, tablets, pills, dragees, powders, granules and the like), the prodrug(s), active ingredient(s) (in their micronized form) is/are mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such as talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered active ingredient(s) moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient(s) therein using, for example, hydroxypropylmethyl cellulose in varying proportions to provide the desired release profile, other polymer matrices, liposomes and/or microspheres. They may be sterilized by, for example, filtration through a bacteria-retaining filter. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient(s) can also be in microencapsulated form.

Liquid dosage forms for oral administration of the active ingredient(s) include pharmaceutically-acceptable emulsions, microemulsions, solutions, suspensions, syrups and elixirs. In addition to the active ingredient(s), the liquid dosage forms may contain inert diluents commonly used in the art, such as, for example, water or other solvents, solubilizing agents and emulsifiers, such as ethyl alcohol, isopropyl alcohol, ethylacetate, butyl alcohol, benzyl benzoate, propylene glycol, glycol, oils (in particular, cottonseed, groundnut, corn, germ, olive, castor and sesame oils), glycerol, amyl alcohol, tetrahydrofuryl polyethylene glycols and fatty acid esters of sorbitan, and mixtures thereof.

Besides inert diluents the oral compositions can also include adjuvants such as wetting agents, emulsifying and suspending agents, sweetening, flavoring, coloring, perfuming and preservative agents. Suspensions, in addition to the active ingredient(s), may contain suspending agents as, for example, ethoxylated alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing the active ingredient(s) with one or more suitable nonirritating excipients or carriers comprising, for example, cocoa butter, polyethylene glycol, wax or salicylate and which is solid at room temperature, but liquid at body temperature and, therefore, will melt in the rectum or vaginal cavity and release the active ingredient(s). Formulations of the present invention which are suitable for vaginal administration also include pessaries, tampons, creams, gels, pastes, foams or spray formulations containing such carriers as are known in the art to be appropriate.

Dosage forms for the topical or transdermal administration of the active ingredient(s) include powders sprays, ointments, pastes, creams, lotions, gels, solutions, patches and inhalants. The active ingredient(s) may be mixed under sterile conditions with pharmaceutically-acceptable carrier, and with any buffers, or propellants which may be required.

The ointments, pastes, creams and gels may contain, in addition to the active ingredient(s), excipients, such as animal and vegetable fats, oils, waxes, paraffins, starch, tragacanth, cellulose derivatives, polyethylene glycols, silicones, bentonites, silicic acid, talc and zinc oxide, or mixtures thereof. Powders and sprays can contain, in addition to the active ingredient(s), excipients such as lactose, talc, silicic acid, aluminum hydroxide, calcium silicates and polyamide powder, or mixtures of these substances. Sprays can additionally contain customary propellants such as chlorofluorohydrocarbons and volatile unsubstituted hydrocarbons, such as butane and propane.

Compounds of the present invention may be administered in intranasal form via topical use of suitable intranasal vehicles, or via transdermal routes, using those forms of transdermal skin patches well known to those of ordinary skill in the art. A transdermal delivery system provides for continuous administration throughout the dosage regimen. Transdermal patches have the added advantage of providing controlled delivery of the active ingredient(s) to the body. Such dosage forms can be made by dissolving, dispersing or otherwise incorporating the active ingredient(s) in a proper medium, such as an elastomeric matrix material. Absorption enhancers can also be used to increase the flux of the active ingredient(s) across the skin. The rate of such flux can be controlled by either providing a rate-controlling membrane or dispersing the active ingredient(s) in a polymer matrix or gel.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Another mode of delivery for the compounds of the present invention may be delivery via the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamide-phenol, polyhydroxy-ethylaspartamide-phenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polyactic and polyglycolic acid, polyepsilon caprolactone, polyhydroxy butyric acid, polyorthoesters, polyacetals, polydihydropyrans, polycyanoacrylates and crosslinked or amphipathic block copolymers of hydrogels.

Pharmaceutical compositions of this invention suitable for parenteral administration comprise the active ingredient(s) in combination with one or more pharmaceutically-acceptable sterile isotonic aqueous or nonaqueous solutions, suspensions or emulsions, or sterile powders which may be reconstituted into sterile injectable solutions or dispersions just prior to use, which may contain antioxidants, buffers, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size, and by the use of surfactants.

These compositions may also contain adjuvants such as wetting agents, emulsifying agents and dispersing agents. It may also be desirable to include isotonic agents, such as sugars, sodium chloride, and the like in the compositions. In addition, prolonged absorption of the injectable pharmaceutical form may be brought about by the inclusion of agents which delay absorption such as aluminum monostearate and gelatin.

In some cases, in order to prolong the effect of the active ingredient(s), it is desirable to slow the absorption of the drug from subcutaneous or intramuscular injection. This may be accomplished by the use of a liquid suspension of crystalline or amorphous material having poor water solubility. The rate of absorption of the active ingredient(s) then depends upon its/their rate of dissolution which, in turn, may depend upon crystal size and crystalline form. Alternatively, delayed absorption of parenterally-administered active ingredient(s) is accomplished by dissolving or suspending the active ingredient(s) in an oil vehicle.

Injectable depot forms are made by forming microencapsule matrices of the active ingredient(s) in biodegradable polymers such as polylactide-polyglycolide. Depending on the ratio of the active ingredient(s) to polymer, and the nature of the particular polymer employed, the rate of release of the active ingredient(s) can be controlled. Examples of other biodegradable polymers include poly(orthoesters) and poly(anhydrides). Depot injectable formulations are also prepared by entrapping the active ingredient(s) in liposomes or microemulsions which are compatible with body tissue. The injectable materials can be sterilized for example, by filtration through a bacterial-retaining filter.

Preferably the composition delivered in the form of an injectable dosage form comprise a biocompatible polymer, a compatible form of the presently disclosed compounds and a biocompatible solvent which solubilizes the biocompatible polymer wherein the weight percents of the biocompatible polymer, the instant and biocompatible solvent are based on the total weight of the complete composition; further wherein sufficient amounts of said polymer are employed in said composition such that, upon delivery to a vascular site, the polymer is able to precipitate and allow release of the active compound in doses sufficient to stop tumor growth.

Still another aspect of this embodiment would observe for appropriate viscosity of said composition, preferably in the range of about 10 to 200 cSt at 40° C.

More preferably, the composition delivered locally to the solid tumor comprises a biocompatible polymer at a concentration of from about 1 to 95 weight percent, active compound at a concentration of from about 5 to about 75 weight percent, and a biocompatible solvent from about 5 to about 95 weight percent, wherein the weight percent of the all components is based on the total weight of the complete composition and further wherein the composition has a viscosity of at least 10 to about 200 and more preferably at last about 200 cSt at 40° C.

Biodegradable polymers are disclosed in the art. For example, Dunn, et al. in U.S. Pat. No. 4,938,763, discloses the following examples of biodegradable polymers: linear-chain polymers such as polylactides, polyglycolides, polycaprolactones, polyanhydrides, polyamides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly (malic acid) poly (amino acids) polyvinylpyrrolidone, polyethylene glycol, polyhydroxycellulose, chitin, chitosan, and copolymers, terpolymers and combinations thereof. Other biodegradable polymers include, for example, gelatin, collagen, etc.

Suitable non-biodegradable biocompatible polymers include, by way of example, cellulose acetates, ethylene vinyl alcohol copolymers, hydrogels (e.g., acrylics), polyacrylonitrile, polyvinylacetate, cellulose acetate butyrate, nitrocellulose, copolymers of urethane/carbonate, copolymers of styrene/maleic acid, and mixtures thereof.

Preferred biocompatible polymers can include acrylic polymers, cellulose diacetate and ethylene vinyl alcohol copolymer, polyethylene glycol, chitosen, collagen and gelatin. Such polymers are either commercially available or can be prepared by art recognized procedures. In a preferred embodiment, the number average molecular weight, as determined by gel permeation chromatography composition is from about 5,000 to about 200,000 more preferably from about 25,000 to about 180,000 and still more preferably from about 50,000 to 100,000.

It is still another aspect of this invention to employ a biocompatible contrast agent within the composition to observe and monitor the clinical progress of the local site of interest. These contrast agents include water soluble contrast agents and water insoluble contrast agents. Preferably, the water insoluble contrast agent is a biocompatible material selected from the group consisting of barium sulfate, tantalum powder and tantalum oxide. In still a further preferred embodiment, the biocompatible solvent is water, dimethylsulfoxide (DMSO), ethanol, ethyl lactate or acetone.

The formulations may be presented in unit-dose or multi-dose sealed containers, for example, ampoules and vials, and may be stored in a lyophilized condition requiring only the addition of the sterile liquid carrier, for example water for injection, immediately prior to use. Extemporaneous injection solutions and suspensions maybe prepared from sterile powders, granules, nanoparticles and tablets of the type described above.

The pharmaceutical compositions of the present invention may also be used in the form of veterinary formulations, including those adapted for the following: (1) oral administration, for example, drenches (aqueous or nonaqueous solutions or suspensions), tablets, boluses, powders, granules or pellets for admixture with feed stuffs, pastes for application to the tongue; (2) parenteral administration, for "ampule, by subcutaneous, intramuscular or intravenous injection as, for example, a sterile solution or suspension or, when appropriate, by intramammary injection where a suspension or solution is introduced into the udder of the animal via its teat; (3) topical application, for example, as a cream, ointment or spray applied to the skin; or (4) intravaginally, for example, as a pessary, cream or foam or any other methods fit to by those of ordinary skill in the art for administration to a region of interest.

Although the present invention has been described with reference to certain embodiments, one skilled in the art will appreciate that the present invention can be practiced by other than the described embodiments, which have been presented for purposes of illustration and not of limitation. Therefore, the scope of the appended claims should not be limited to the description of the embodiments contained herein.

The general methods given in Schemes 1, 2, and 3 for the preparation of compounds exemplified in Tables I, II, and III above of the present invention are further illustrated by the following examples. Specifically, the methods given in Schemes 1 and 2 for the preparation of 6-alkoxyalkyl Estradiol compounds are illustrated by Examples 1-5 shown below, and Scheme 3 is for the preparation of 6-amino derivatives of estradiol. An example of assessing the estrogen receptor binding capacity is articulated in example 4, and finally assessing the $IC_{50}$ of the preferred compounds of the instant invention and their comparative efficacy is given in example 5. Unless otherwise specified all starting materials and reagents are of standard commercial grade, and are used without further purification, or are readily prepared from such materials by routine methods. Those skilled in the art of organic synthesis will recognize that starting materials and reaction conditions may be varied to achieve the desired end product.

EXAMPLE 1

Methods of Preparing
6-hydroxymethyl-androsta-1,4-diene-3,17 dione

In a reaction system, sufficient amounts of (+)androsta-1, 4-diene-3,17-dione (ADD), 12.2 equivalents pyrrolidine, catalytic acetic acid, denatured ethanol (95/5 ethanol/methanol) and 6-7% tetrahydrofuran (THF) were heated to 30 to 40° C. for a minimum of 16 hours to form 1,3-dipyrrolidinoandrosta-3,5-diene-17one. Once the ADD content reaches to a less than 3% by HPLC area, or it becomes static or the resulting dipyrrolidinoandrostadiene begins to revert to ADD, the reaction mixture is cooled to 5±5° C. The resulting compound is then collected and washed with cold denatured ethanol. Yields are typically 70-80% on a dry basis with purities typically 90-95% by HPLC area percent.

The resulting 1,3-dipyrrolidinoandrosta-3,5-diene-17one is then mixed in amount of 1 equivalent, with 2.6 equivalents formalin (formaldehyde) in 10 ml dichloromethane/g at room temperature. The reaction mixture is then acidified to a pH of about 2 with 2% sulfuric acid solution. Accordingly, an organic layer is formed, which is washed with 2% sulfuric acid and 1:1 water/brine. Solvent exchange into toluene (approximately 10 ml/g) is then carried out wherein the product crystallizes as toluene exchange traspires. Said product is collected washed and dried to provide 6-hydroxymethyl-androsta-1,4-diene-3,17 dione. One of ordinary skill in the art can further modify the stereochemistry at position 6, if so desired by employing known techniques in the art.

EXAMPLE 2

Methods of Preparing Compound NDC-1022 and NDC-1033

As outlined in Scheme 2, estradiol derivatives NDC-1022, NDC-1033 were synthesized in the following manner. The protected estradiol compound 2 is prepared by reaction of compound 1 with dihydropyran in THF, using toluenesulfonic acid or camphorsulfonic acid as catalyst. As one of ordinary skill in the art can appreciate this reaction is an equilibrium reaction and would not go to completion under such conditions. Thus, both the mono-protected estradiols can be found in the reaction mixture. Such crude reaction mixture would undergo a trituration step with acetonitrile causing the desired bis-THP estradiol to crystallize in approximately 70% yield.

As shown in Scheme 2, the key intermediate compound 3 is obtained via acylation at the benzylic 6-position with the strong base mixture referred to as LiDAKOR: butyl lithium, diisopropylamine, and potassium tert-amylate. Under such conditions at −70° C., one of ordinary skill in the art can appreciate the abstraction of a proton at a benzylic position. The intermediate compound 3 is then purified by column chromatography to give a syrup in approximately 50% yield, still containing minor impurities and column solvents. Reduction of the aldehyde with an excess of lithium aluminum hydride results in high yields of the racemic hydroxymethyl estradiol compound 4 as a glassy foam.

For purposes of preparing NDC-1022 and NDC 1033, the methoxymethyl intermediate compound 7 was prepared by methylation of compound 4 with sodium hydride and methyl iodide. Compound 7 was purified by column chromatography to give a glassy foam. Deprotecting the protected groups would give racemic 6-methoxymethyl estradiol compound 8. Separation of the enantiomers was performed using chiral preparative HPLC to give the compounds NDC-1022 and NDC-1033. For compound NDC-1022, a chiral purity of >95:5 R:S was realized. For compound NDC-1033, a chiral purity of 86:14 S:R was realized. It is well within the level of one of ordinary skill in the art to employ NMR for determination of the absolute stereochemistry of the 6-position, where the 4- and 6-protons are diagnostic.

EXAMPLE 3

Methods of Preparing NDC-1055 and NDC-1066

Using the same methodologies described in Example 2, compound 4 is synthesized. Deprotection of compound 4 was then achieved with catalytic hydrogen chloride in methanol, and racemic compound 5 was separated on chiral preparative HPLC to give two fractions, one enriched for NDC-1055 and the other enriched for NDC-1066. For each compound, chiral purity of >95:5 R:S and S:R was realized respectively. Absolute stereochemistry of the 6-position was established by NMR, where the 4- and 6-protons are diagnostic.

EXAMPLE 4

Methods of determining estrogen receptor binding capacity using Luciferase activity.

Estrogen receptor-negative CV-1 kidney cells were maintained in Dulbecco's modified Eagle's medium with 4.5 g/L glucose supplemented with 10% fetal bovine serum and 100 units/ml penicillin-streptomycin at 37° C. in a humidified 5% $CO_2$ atmosphere. The cells were then plated in 6-well dishes at a density of $2\times10^5$ cells per well in phenol-red free Dulbecco's modified Eagle's medium containing 10% charcoal-dextran-stripped fetal bovine serum. CV-1 cells were transfected using LipofectAMINE reagent according to the manufacturer's protocol. Transfections containing 1.5 ug of reporter plasmid (containing ERE-tk-luciferase containing a single ERE cloned upstream of the thymidine kinase promoter and luciferase gene) and 0.5 ug of either ERα or ERβ expression vector (containing CMV-ERα or CMV-ER$_β$ full length coding sequence respectively). The next day, cells received no treatment (controls) or were treated with estradiol alone (1 nM) or estradiol plus an Endece compound (at varying concentrations). After 16-24 hours, cells were harvested and assayed for luciferase activity.

At the outset, cell monolayers were washed twice with ice-cold phosphate-buffered saline and incubated for 15 minutes in 250 ul of 1× cell culture lysis reagent (Promega, Madison, Wis.). Cell extracts were transferred to a fresh tube and assayed using the luciferase assay system (Promega). For each assay, 10 ul of extract was diluted with 90 ul of 1× cell culture lysis reagent. Luminescence was read using an AutoLumat LB953 luminometer.

A compound or a salt thereof, which is identified by the binding assay described herein is a compound that inhibits the binding of estrodial at the ligand binding site of the estrogen receptors. Specifically, it is a compound or a salt thereof that is envisioned to cause cell proliferation statasis and accordingly exerts its pharmacological activity. As indicated in FIGS. 3 and 4, lead compounds NDC-1022, NDC-1033 exhibit strong competitive behavior against estradiol in binding to either of the estrogen receptors thereby causing stasis of cell proliferation activity.

EXAMPLE 5

Method of determining the $IC_{50}$ values of the candidate compounds. The cell lines listed were maintained at approximately 5% $CO_2$, 37° C., 95% relative humidity in the media appropriate for that cell line. The cells were sub-cultured every two to three days and plated in clear bottom 96-well plates at a density of $1\times10^4$ cells/well and incubated at ca. 5% $CO_2$, 37° C. overnight prior to initiation of the assay. To begin cell viability assays, the media in the cell plate (100 μL) was replaced with fresh media (100 pL). The test articles were serially diluted 1:2 in fresh media in duplicate and added to the cells (100 μL) at final sample concentrations of 0.46, 1.37, 4.12, 12.35, 37.04, 111.1, 333.3 and 1000 μM ($\leq$1% DMSO) in a total volume of 200 μL. Wells containing no cells and wells containing cells lysed with 0.1% Triton-X were used for baseline controls. Tamoxifen was used as a known control for each assay and DMSO only will be run as vehicle control. The samples were incubated at ca. 37° C. in humidified 5% $CO_2$ atmosphere for 72 hours. The plate was monitored once a day during the incubation period, paying special attention to the level of confluence. If the cells approach confluence prior to the end of the 72 hour incubation period the experiment was terminated at that time and cell viability measured as described below.

Cell Viability was determined using a commercially available kit to determine ATP levels by luminescence. Briefly, the cell plate had the media removed and replaced with 100 μL of fresh media, and the buffer and lyophilized substrate were equilibrated to room temperature. The buffer was used to reconstitute the substrate just prior to addition to the wells of the cell plate (100 μL per well). The plate was placed into the Infinite M200 plate reader, allowed to shake for 10 minutes followed by a 10 minute wait period, the plate was read using an integration time of 0.5 sec with no attenuation.

The mean baseline controls (wells with Triton X-100 or no cells) were subtracted from the total luminescence to give the net luminescence for that well. This total was compared to the control of DMSO only. An $IC_{50}$ was calculated as the concentration that led to a response of 50% compared to the vehicle control cells. FIGS. 5 and 6 depict the results of the tests. Accordingly, those of ordinary skill in the art can appreciate that the R configuration of the instantly claimed composition are superior to other stereoisomers.

EXAMPLE 6

Methods of Preparing NDC-1187

Using the same methodologies as in examples 1-2, NDC 1022 is prepared. To a solution of NDC-1022 (0.32 g, 1 mmol) in DCM (30 ml) acetic anhydride (0.6 ml, 6 mmol, 3 eq), TEA (0.5 ml, 3.6 mmol, 1.8 eq) and DMAP (50 mg) was added. The reaction solution was stirred at ambient temperature for 3 hrs. Thin Layer Chromatography ("TLC") followed the reaction.

The reaction solution was washed with 1M HCl (20 ml), Saturated $NaHCO_3$ (20 ml) and brine (20 ml) respectively. The DCM phase was dried over MgSO4 and filtered. The filtrate was evaporated and dried in high vacuum at 60° C. for 3 hrs and at ambient temperature overnight to afford pure desired compound 1 of Scheme 3 (0.4 g, white, quantitative).

EXAMPLE 7

To a solution of compound 2 of Scheme 3 (0.35 g, 0.87 mmol) in DCM was added iodotrimethylsilane (6 ml, 44 mmol, eq) at ambient temperature. The yellow solution was stirred at 38° C. overnight under argon.

The reaction solution was cooled in an ice-bath. To it was added excess sat. $NaHCO_3$ (10 ml) slowly to quench the reaction. After separation of the mixture, the organic phase was washed with brine and concentrated for silica gel purification using 3% MeOH in DCM as mobile phase. Yielded 270 mg of pure compound 2 of Scheme 3 (80%).

A solution of compound 2 of Scheme 3(250 mg, 0.65 mmol), triphenylphosphine (222 mg, 0.85 mmol, 1.3 eq), N-hydroxyphthalimide (140 mg, 0.85 mmol, 1.3 eq) in THF (20 ml) was cooled in an ice-batch. To the cooled solution was added diethyl azodicarboxylate (0.6 ml, 1 mmol, 1.5 eq). The reaction mixture was wormed to ambient temperature and stirred overnight.

The reaction mixture was evaporated, and the resulting residue was diluted with DCM (50 ml). It was washed with brine and concentrated for silica gel purification using 3% MeOH/DCM as mobile phase to yield 260 mg of desired white compound 3 of Scheme 3 (75%). The syntheses from step 1 to step 3 may be repeated to prepare another batch of compound 3 of Scheme 3 (580 mg).

EXAMPLE 8

A solution of compound 3 of Scheme 3(580 mg, 1.1 mmol) in anhydrous DCM (30 ml) was cooled in an ice-batch. Methyl hydrazine (0.22 ml, 2.2 mmol, 4 eq) was added. The mixture was wormed to ambient temperature and stirred for 3 hrs. LC-MS followed the reaction.

The reaction solution was washed with a solution of brine and Sat. $NaHCO_3$ (1:1, 10 ml). The aqueous phase was washed with DCM (10 ml). The combined DCM phases were evaporated to dryness under high vacuum. LC-MS confirmed that the crude product contained tow major products of compound 4 and compound 4a of Scheme 3. The crude mixture was used directly for next reaction without further purification.

EXAMPLE 9

The crude mixture (~0.7 mmol) of compounds 4 and 4a of Scheme 3 in MeOH (60 ml) was cooled in an ice-bath. To it was added a solution of sodium carbonate (0.5 g, 4.7 mmol) in water (10 ml), and then added another solution of NaOH (0.8 g, 20 mmol) in water (10 ml). It was wormed to ambient temperature and stirred overnight.

The pH of final reaction solution was about 14. A solution of sat. sodium bicarbonate (~10 ml) was added to adjust pH to 10. The mixture was evaporated to remove most of methanol. To the resulting mixture were added DCM (100 ml) and sat. sodium bicarbonate (30 ml) for extraction. The aqueous phase was washed with DCM (2×50 ml). The combined DCM phases were evaporated to dryness to give crude mixture 400 mg.

The crude mixture was purified by silica gel column using 5% MeOH/DCM as mobile phase to afford desired final product NDC-1187 (135 mg, off white, 60% yield, 98% HPLC purity, NMR and LC-MS confirmed).

Scheme 2- Alternative methods for preparing the compounds of the invention.
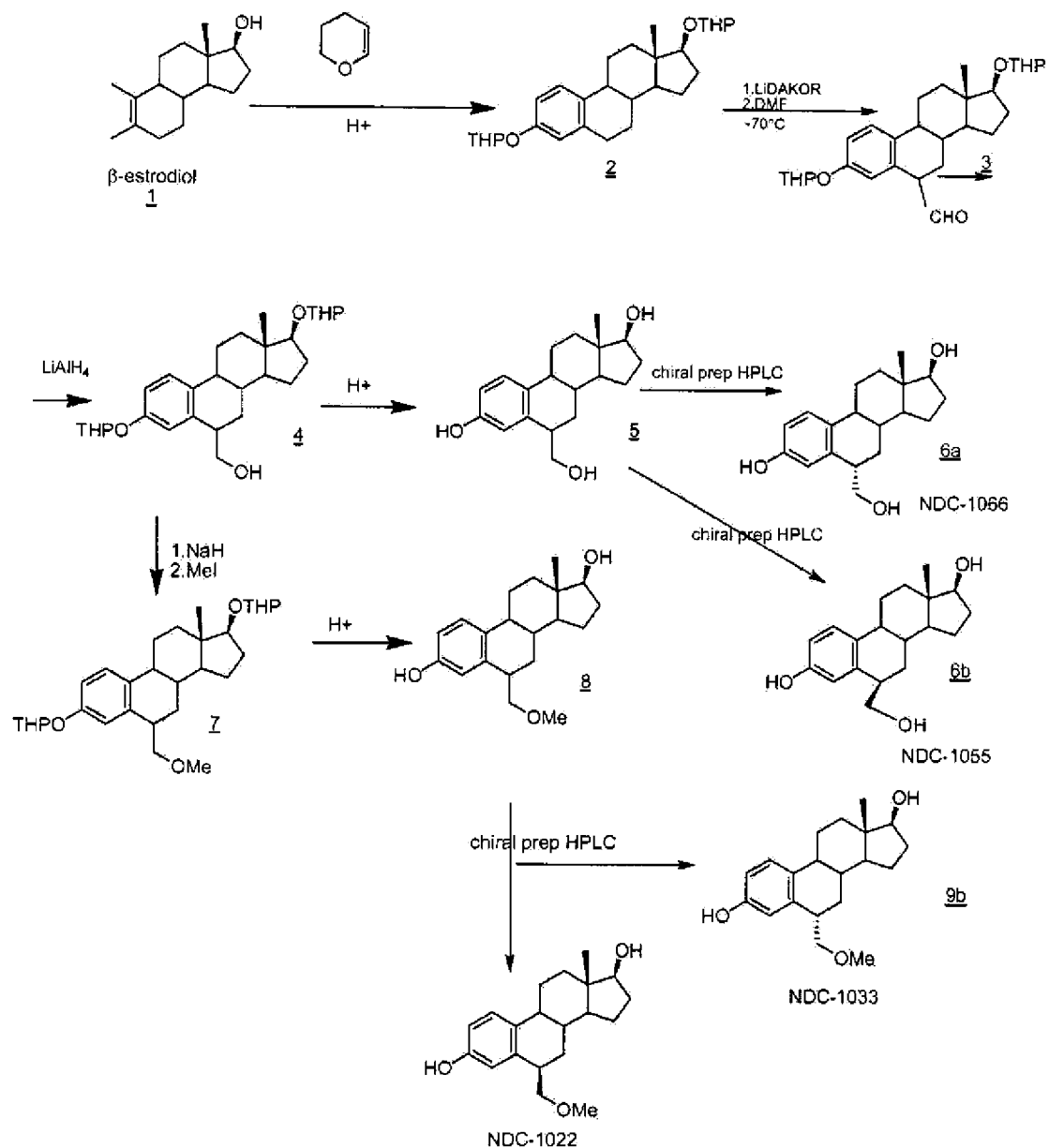

I claim:

1. A compound of the structure:

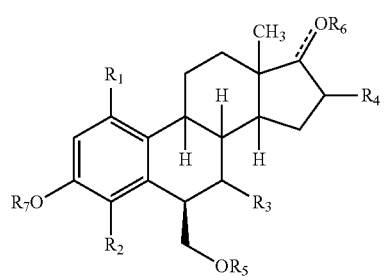

wherein:

R$_1$, R$_2$, R$_3$, R$_4$ are independently selected from the group consisting of H, C$_1$-C$_6$ alkyl, substituted alkyl, and halogen;

R$_5$ is selected from the group consisting of —NH$_2$, —NH(CH$_2$)$_n$OH, —NH(CH$_2$)$_n$—COOsalt, —(NH)CH$_2$OHCH$_3$, —NHCOOH, and —CH$_2$NHCOOH;

n is an integer from 1-7;

R$_6$ is selected from a group consisting of H, a C$_1$-C$_6$ alkyl, a C$_1$-C$_6$ substituted alkyl, a sulfate, a glucoronide, a phenyl or a substituted phenyl group, a cyclo- or heterocyclo group, and R$_7$ is selected from the group consisting of H, a C$_1$-C$_6$ alkyl, a C$_1$-C$_6$ substituted alkyl, a halogen, a halogenated alkyl, a sulfate, a glucoronide, —SO$_2$NH$_2$, —COOH, —CN, —CHO, —COO salt and —NH$_2$; and wherein the ═ symbol represents either a single or a double bond with the proviso that when the ═ symbol is a double bond and forms a keto group at position 17, then no R$_6$ is present.

2. The compound of claim 1 of the formula:

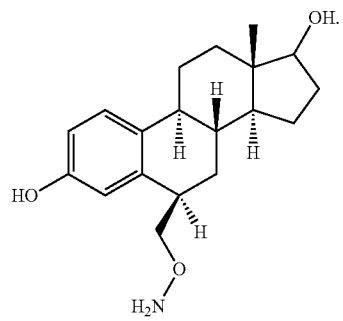

3. A pharmaceutical composition comprising the compound of claim 1 and a pharmaceutically-acceptable carrier, wherein said compound comprises at least one S enantiomer, R enantiomer, S diasteromer or R diasteromer.

* * * * *

UNITED STATES PATENT AND TRADEMARK OFFICE
CERTIFICATE OF CORRECTION

PATENT NO. : 8,168,621 B2
APPLICATION NO. : 12/132857
DATED : May 1, 2012
INVENTOR(S) : James Yarger It is certified that error appears in the above-identified patent and that said Letters Patent is hereby corrected as shown below:

In the specification:
Cols. 21 and 22

Replace Scheme 2 as printed with the Scheme 2 depicted below in order to correct errors within Scheme 2 as printed.

Signed and Sealed this
Twenty-sixth Day of March, 2013

Teresa Stanek Rea
*Acting Director of the United States Patent and Trademark Office*